United States Patent
Priebe

(10) Patent No.: US 8,535,642 B2
(45) Date of Patent: Sep. 17, 2013

(54) CONTRAST AGENTS

(75) Inventor: Hanno Priebe, Oslo (NO)

(73) Assignee: GE Healthcare AS, Oslo (NO)

(*) Notice: Subject to any disclaimer, the term of this patent is extended or adjusted under 35 U.S.C. 154(b) by 192 days.

(21) Appl. No.: 12/919,493

(22) PCT Filed: Feb. 26, 2009

(86) PCT No.: PCT/EP2009/052245
§ 371 (c)(1),
(2), (4) Date: Aug. 26, 2010

(87) PCT Pub. No.: WO2009/106552
PCT Pub. Date: Sep. 3, 2009

(65) Prior Publication Data
US 2011/0052504 A1    Mar. 3, 2011
US 2012/0039815 A9    Feb. 16, 2012

Related U.S. Application Data

(60) Provisional application No. 61/091,459, filed on Aug. 25, 2008.

(30) Foreign Application Priority Data

Feb. 27, 2008 (EP) .................................. 08003563

(51) Int. Cl.
*A61K 49/04*    (2006.01)
*A61K 49/00*    (2006.01)

(52) U.S. Cl.
CPC ...................................... *A61K 49/04* (2013.01)
USPC ............................................ 424/9.1; 424/9.4

(58) Field of Classification Search
None
See application file for complete search history.

(56) References Cited

U.S. PATENT DOCUMENTS

| 3,763,226 A |  | 10/1973 | Ingelman |  |
|---|---|---|---|---|
| 5,349,085 A | * | 9/1994 | Hansen et al. | 564/153 |
| 5,866,100 A |  | 2/1999 | Tournier et al. |  |
| 2005/0113675 A1 | * | 5/2005 | Aime et al. | 600/420 |

FOREIGN PATENT DOCUMENTS

| EP | 0108638 | 5/1984 |
| EP | 0177414 | 4/1986 |
| GB | 1360553 | 7/1974 |
| WO | 94/14478 | 7/1994 |
| WO | 96/09282 | 3/1996 |
| WO | 2007/094677 | 8/2007 |

OTHER PUBLICATIONS

PCT/EP2009/052245 ISRWO Dec. 22, 2009.

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention relates to a class of compounds and to diagnostic compositions containing such compounds where the compounds are iodine containing compounds. More specifically the iodine containing compounds are chemical compounds containing two linked iodinated phenyl groups of the general formula R—N(CO—CH$_3$)—X—N(CO—CH$_3$)—R and salts or optical active isomers thereof, wherein X denotes a divalent linking moiety with 5 to 10 bridge elements of carbon, oxygen, sulphur and nitrogen separating the acetylated nitrogen atoms, and which may be further substituted by hydroxyl groups, by $C_1$ to $C_4$ alkyl moieties optionally substituted by hydroxyl groups, by $C_1$ to $C_4$ alkoxy groups, by amino groups and by $C_1$ to $C_4$ alkylamino groups, and wherein 2 or 3 carbon bridge elements together with alkyl or alkoxy groups form a cyclopentane, cyclohexane, pentahydropyran or tetrahydrofuran entity which may be alkyl- or hydroxyalkyl-substituted and each R denotes a triiodinated phenyl residue further substituted by hydrophilic moieties. The invention also relates to the use of such diagnostic compositions as contrast agents in diagnostic imaging and in particular in X-ray imaging, and to contrast media containing such compounds.

7 Claims, No Drawings

CONTRAST AGENTS

This application is a filing under 35 U.S.C. 371 of international application number PCT/EP2009/052245, filed Feb. 26, 2009, which claims priority to European application number 08003563.7 filed Feb. 27, 2008 and U.S. application No. 61/091,459 filed Aug. 25, 2008, the entire disclosure of each of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing two linked iodinated phenyl groups.

The invention also relates to the use of such diagnostic compositions as contrast agents in diagnostic imaging and in particular in X-ray imaging, and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™) nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in mg iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

In patients with acute renal failure, nephropathy induced by contrast medium remains one of the most clinically important complications of the use of iodinated contrast medium.

Aspelin, P et al, The New England Journal of Medicine, Vol. 348:491-499 (2003) concluded that nephropathy induced by contrast medium may be less likely to develop in high risk patients when iodixanol is used rather than a low-osmolar, non-ionic contrast medium.

The part of the patient population considered as high risk patients is increasing. To meet the need for continuous improvement of in vivo X-ray diagnostic agents for the entire patient population, there is a continuous drive in finding X-ray contrast agents that has improved properties, also with regards to contrast induced nephrotoxicity (CIN).

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/011094 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Relevant patent publications comprises EP 1186305, EP 686046, EP108638, EP 0049745, EP 0023992, WO 2003080554, WO2000026179, WO 1997000240, WO 9208691, U.S. Pat. Nos. 3,804,892, 4,239,747, 3,763,226, 3,763,227 and U.S. Pat No. 3,678,152.

In particular, EP 108638 describes a small group of non-ionic dimers where the two triiodinated phenyl groups are linked by linking groups of the formulas —N(COCH$_3$)—CH$_2$—CH(OH)—CH$_2$—(COCH$_3$)N— and —N(COCH$_3$)—CH$_2$—CH(OH)—CH(OH)—CH$_2$—(COCH$_3$)N—, and wherein the carboxamide substituents of the triiodinated phenyl groups contain either two —CH(CH$_2$—OH)$_2$ groups or two —CH$_2$—CH(OH)—CH$_2$—OH groups. Four compounds, denoted A, B, C and D are prepared, of which compound A is known under the INN name of iodixanol.

At this time, one contrast medium having an iodinated non-ionic dimer as the active pharmaceutical ingredient is on the market, the product Visipaque™ containing the compound iodixanol mentioned above. The compound Hexabrix™, containing the ionic dimeric compound ioxaglic acid is also on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose and any additional adverse effect known or discovered for such iodinated compounds.

SUMMARY OF THE INVENTION

The present invention provides compounds useful as contrast media having improved properties over the known media with regards to at least one of the criteria mentioned above and in particular to renal toxicity, osmolality, viscosity and solubility. The contrast media comprises iodine containing contrast enhancing compounds where the iodine containing compounds are chemical compounds containing two linked iodinated phenyl groups. The iodine containing contrast enhancing compounds can be synthesized from commercially available and relatively inexpensive starting materials.

DETAILED DESCRIPTION OF THE INVENTION

The new compounds of the invention, diagnostic compositions comprising the compounds, and their use as X-ray contrast agents, are specified in the attached claims and in the specification hereinafter.

The contrast enhancing compounds are synthetic chemical compounds of formula (I)

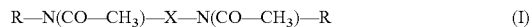

Formula (I)
and salts or optical active isomers thereof,
wherein
X denotes a divalent linking moiety with 5 to 10 bridge elements of carbon, oxygen, sulphur and nitrogen separating the acetylated nitrogen atoms and which may be further substituted by hydroxyl groups, by C$_1$ to C$_4$ alkyl moieties optionally substituted by hydroxyl groups, by C$_1$ to C$_4$ alkoxy groups, by amino groups and by C$_1$ to C$_4$ alkylamino groups, and wherein 2 or 3 carbon bridge elements together with alkyl or alkoxy groups form a cyclopentane, cyclohexane, pentahydropyran or tetrahydrofuran entity which may be alkyl- or hydroxyalkyl-substituted and each R independently are the same or different and denote a triiodinated phenyl group, preferably a 2,4,6-triiodinated phenyl group further substituted by two groups R$^1$ wherein each R$^1$ are the same or different and denote a hydrogen atom or a non-ionic hydrophilic moiety, provided that at least one R$^1$ group in the compound of formula (I) is a hydrophilic moiety.

The bridging group X in formula (I) above may more specifically denote a straight alkylene moiety with 5 to 10 carbon atom separating the acetylated nitrogen atoms. The C$_5$ to C$_{10}$ alkylene moiety is preferably substituted by one to four hydroxyl groups, and in addition up to 4 carbon atoms of the $C_5$ to $C_{10}$ alkylene moiety may be replaced by oxygen atoms. Preferably none of the hydroxyl groups are on carbon atoms vicinal to a nitrogen atom.

When the bridging group X comprises a cyclic group element, this is preferably a heterocyclic group element such as pentahydropyrane.

Still more preferred the divalent linker group X comprises a straight alkylene moiety with 5 to 10 carbon atom substituted by 2 or 3 hydroxy groups where none of the hydroxyl groups are on a carbon atom vicinal to the bridge nitrogen atom. Examples of preferred hydroxylated alkylene groups are the 2,4-dihydroxy-pentylene, 2,3,4-trihydroxy-pentylene and 2,7-dihydroxy-octylene moieties.

Also preferred are the divalent linker groups X comprising a straight alkylene moiety wherein 1 or 2 of the 5 to 10 carbon atoms are replaced by oxygen atoms and where the linker may be further substituted by 2 or 3 hydroxy groups where none of the hydroxyl groups are on a carbon atom vicinal to a nitrogen atom. Examples of preferred divalent linker groups are 2,6-dihydroxy-4-oxa-heptylene and 2,9-dihydroxy-4,7-dioxa-decylene.

Each of the iodinated R groups can be the same or different and preferably denote a 2,4,6-triiodinated phenyl group, further substituted by two groups $R^1$ in the remaining 3 and 5 positions in the phenyl moiety.

The non-ionic hydrophilic moieties may be any of the non-ionizing groups conventionally used to enhance water solubility. Hence, the $R^1$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or CH moieties replaced by oxygen or nitrogen atoms. The $R^1$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^1$ substituents are the same or different and are mono or polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage, preferably carbamoyl linkages.

The $R^1$ groups of the formulas listed below are particularly preferred:

—CONH—CH$_2$—CH$_2$—OH;

—CONH—CH$_2$—CHOH—CH$_2$—OH;

—CON(CH$_3$)CH$_2$—CHOH—CH$_2$OH;

—CONH—CH—(CH$_2$—OH)$_2$;

—CON—(CH$_2$—CH$_2$—OH)$_2$;

—CONH$_2$;

—CONHCH$_3$;

—CONH—CH$_2$—CH$_2$—O—CH$_3$;

—CONH—O—CH$_3$;

—CONH—CH$_2$—CHOH—CH$_2$—O—CH$_3$;

—CONH—CH$_2$—CHOCH$_3$—CH$_2$—OH;

—CON(CH$_2$—CHOH—CH$_2$—OH)(CH$_2$—CH$_2$—OH);

—CONH—C(CH$_2$—OH)$_2$CH$_3$;

—CONH—C(CH$_2$—OH)$_3$;

—CONH—CH(CH$_2$—OH)(CHOH—CH$_2$—OH);

—NHCOCH$_2$OH;

—N(COCH$_3$)H;

—N(COCH$_3$)C$_{1-3}$ alkyl;

—N(COCH$_3$)—mono, bis or tris-hydroxy C$_{1-4}$ alkyl;

—N(COCH$_2$OH)—hydrogen, mono, bis or tris-hydroxy C$_{1-4}$ alkyl;

—N(CO—CHOH—CH$_2$OH)—hydrogen, mono, bis or trihydroxylated C$_{1-4}$ alkyl;

—N(CO—CHOH—CHOH—CH$_2$OH)—hydrogen, mono, bis or trihydroxylated C$_{1-4}$ alkyl;

—N(CO—CH—(CH$_2$OH)$_2$)—hydrogen, mono, bis or trihydroxylated C$_{1-4}$ alkyl; and

—N(COCH$_2$OH)$_2$.

Even more preferably the $R^1$ groups will be equal or different and denote one or more moieties of the formulas —CONH—CH$_2$—CHOH—CH$_2$—OH, —CON(CH$_3$) CH$_2$—CHOH—CH$_2$—OH, —CONH—CH—(CH$_2$—OH)$_2$, —CON—(CH$_2$—CH$_2$—OH)$_2$, and —CONH—CH$_2$—CH$_2$—OH. It will be understood that in each of the two groups R in formula (I) each of the two $R^1$ substituents may be the same or different.

Still more preferably both R groups are the same and the $R^1$ groups in each R are the same or different and have the meanings above.

Thus, preferred structures according to the invention include the compounds of formula (II):

R—N(CO—CH$_3$)—CH$_2$—CH(OH)—CH$_2$—CH(OH)—CH$_2$—N(CO—CH$_3$)—R  (IIa)

R—N(CO—CH$_3$)—CH$_2$—CH(OH)—CH(OH)—CH(OH)—CH$_2$—N(CO—CH$_3$)—R  (IIb)

R—N(CO—CH$_3$)—CH$_2$—CH(OH)—CH$_2$—CH$_2$—CH$_2$—CH$_2$—CH(OH)—CH$_2$—N(CO—CH$_3$)—R  (IIc)

R—N(CO—CH$_3$)—CH$_2$—CH(OH)—CH$_2$—O—CH$_2$—CH(OH)—CH$_2$—N(CO—CH$_3$)—R  (IId)

R—N(CO—CH$_3$)—CH$_2$—CH(OH)—CH$_2$—O—CH$_2$—CH$_2$—O—CH$_2$—CH(OH)—CH$_2$—N(CO—CH$_3$)—R  (IIe)

Formula (II)

In formulas (II) each group R has the meaning above, more preferably both iodophenyl groups R are the same and the $R^1$ groups all denote non-ionic hydrophilic moieties, and preferably the $R^1$ groups are linked to iodinated phenyl moiety by carbamoyl linkages.

Some preferred examples the structures according to the invention include the compounds of formulas (IIIa) to (IIIq) below.

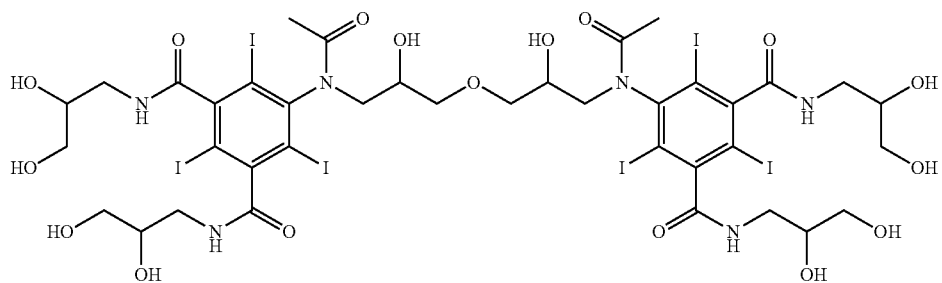
Formula (IIIa)
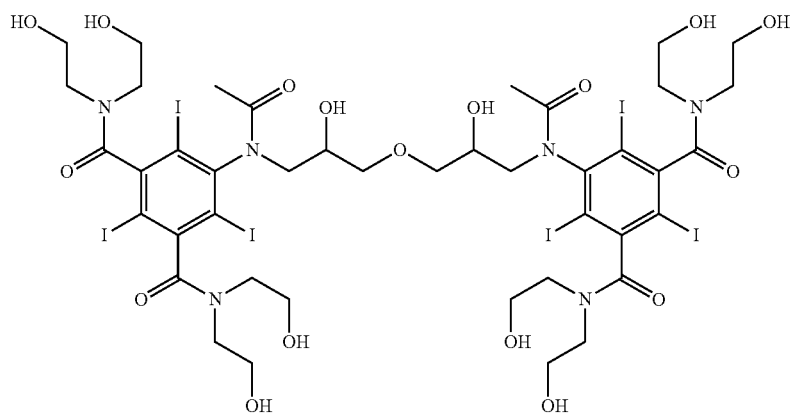
Formula (IIIb)
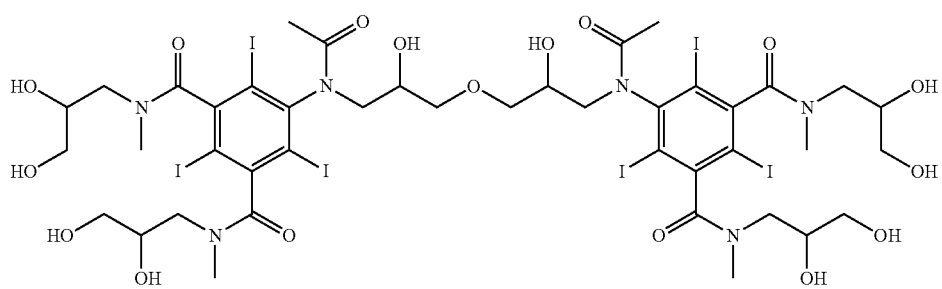
Formula (IIIc)
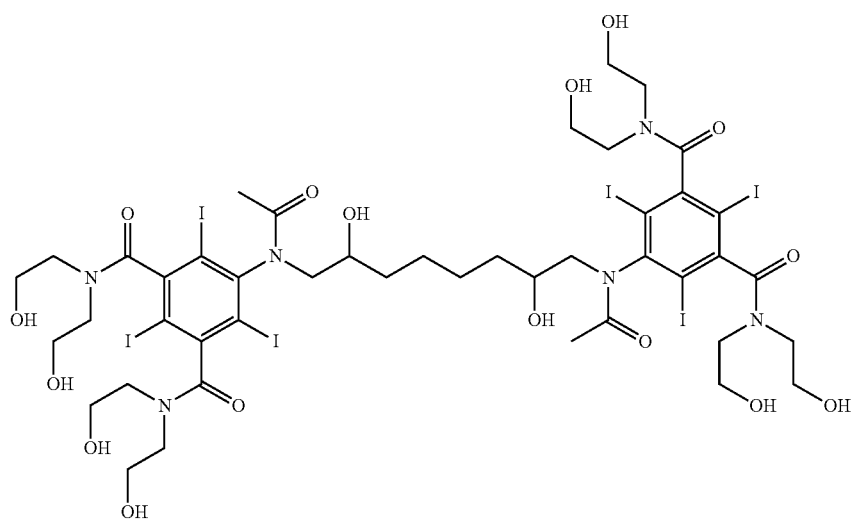
Formula (IIId)

Formula (IIIe)
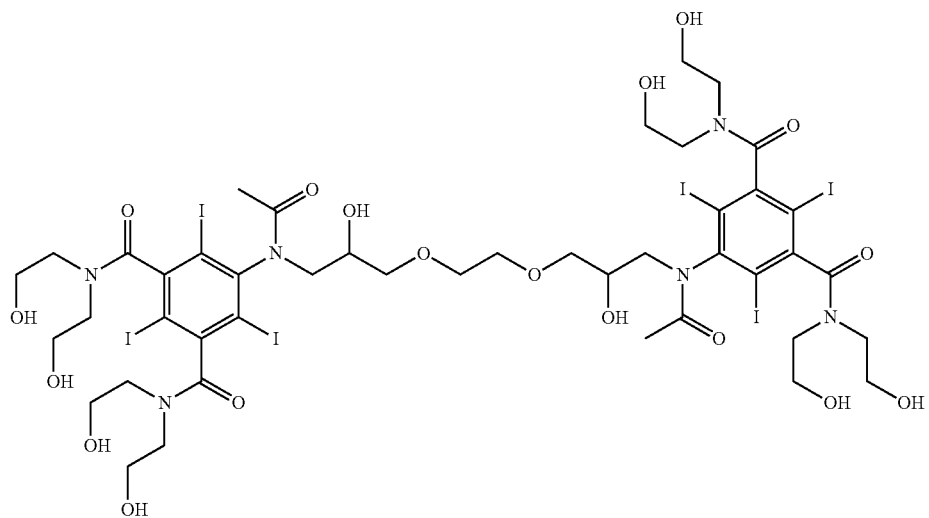
Formula (IIIf)
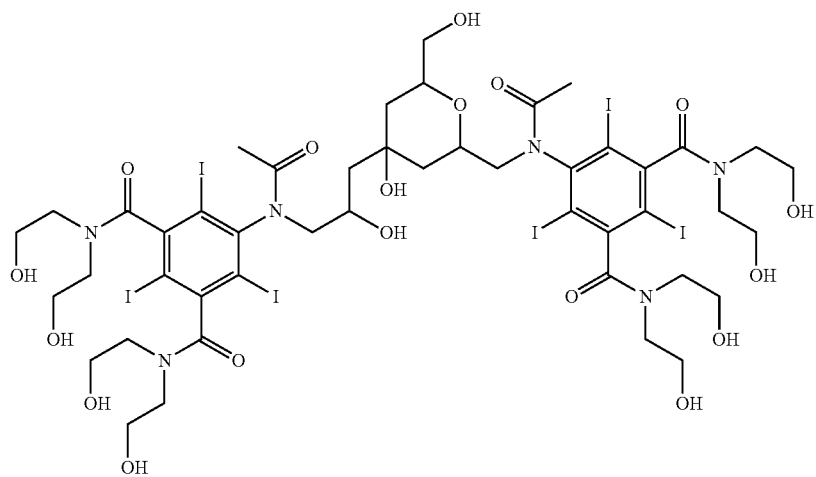
Formula (IIIg)
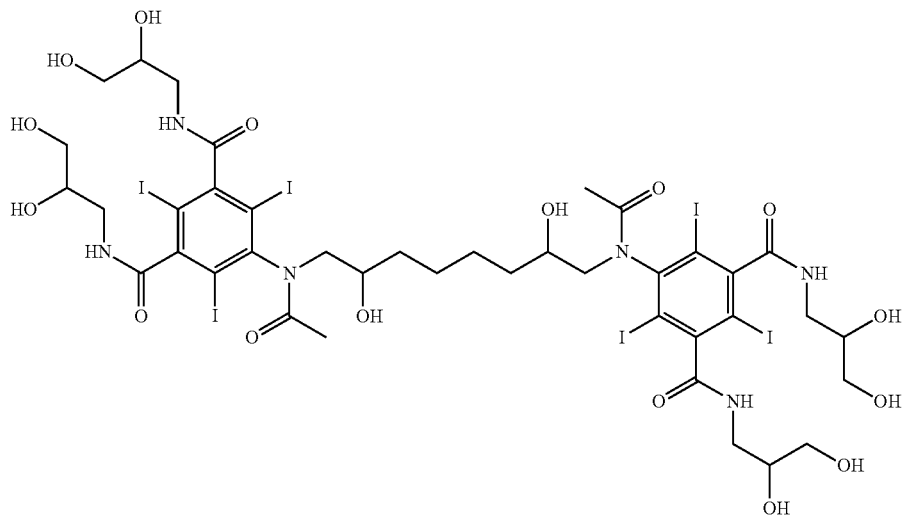

-continued
Formula (IIIh)
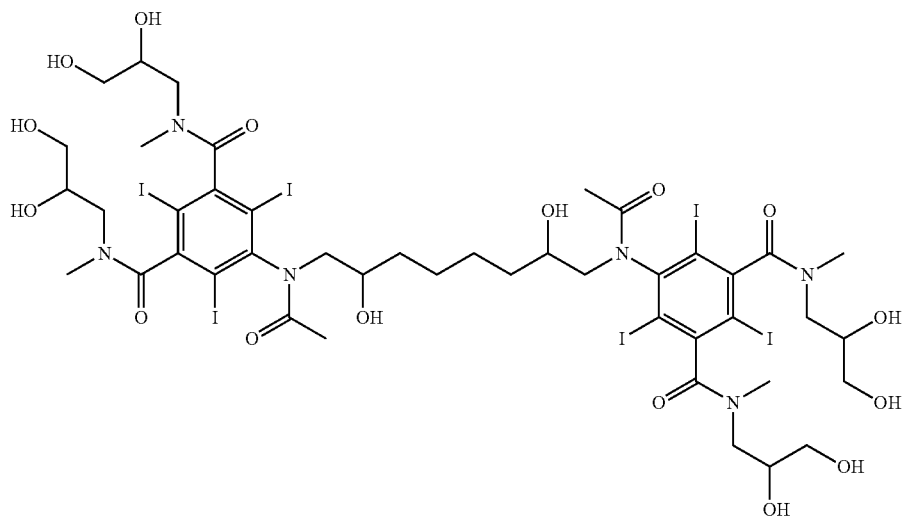
Formula (IIIi)
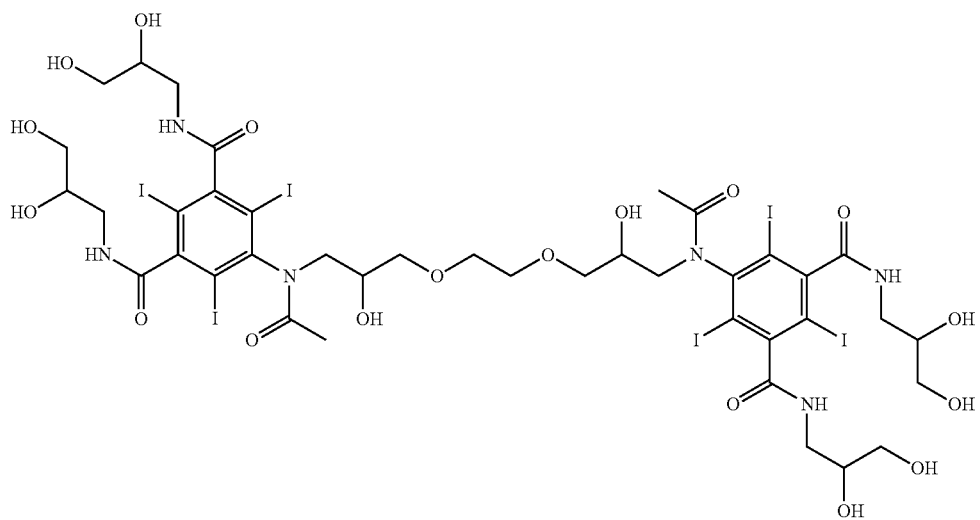
Formula (IIIj)
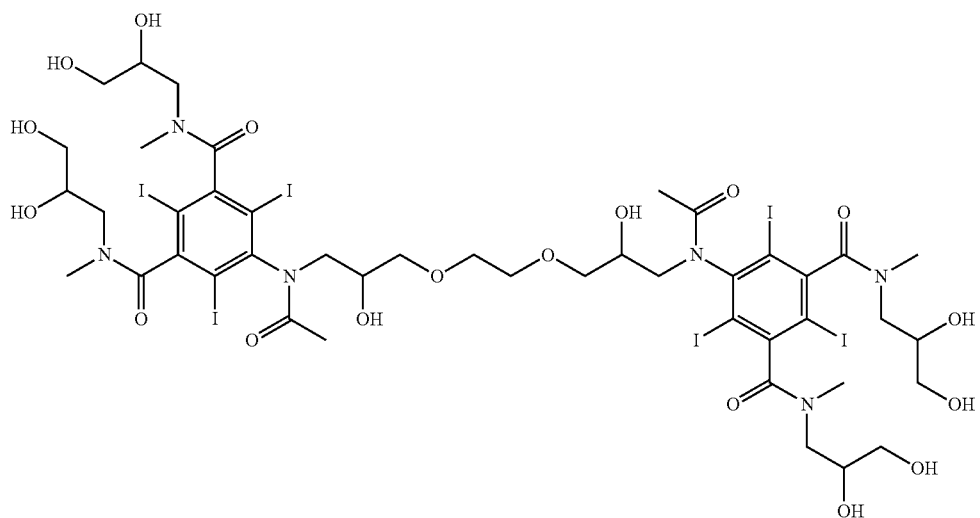

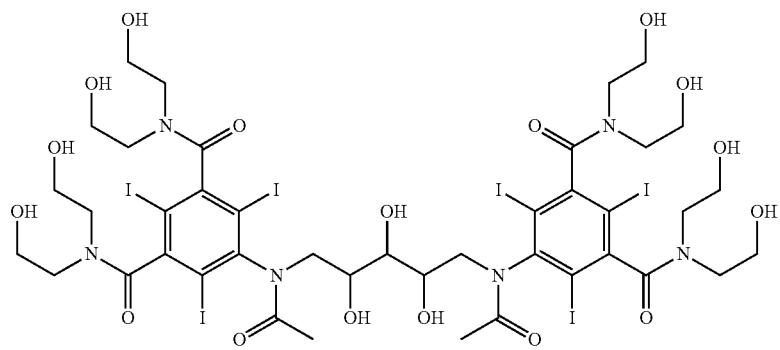
Formula (IIIk)
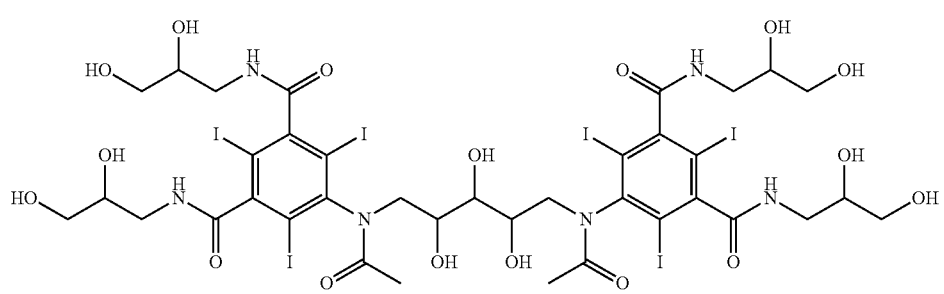
Formula (IIIl)
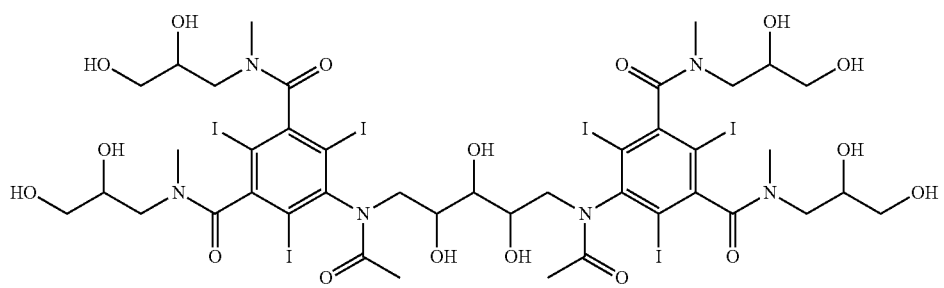
Formula (IIIm)
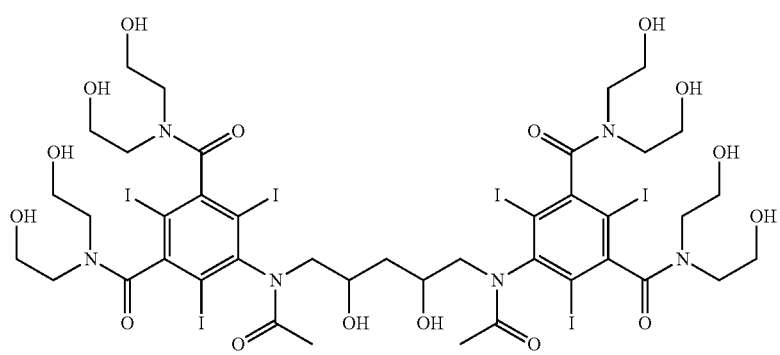
Formula (IIIn)
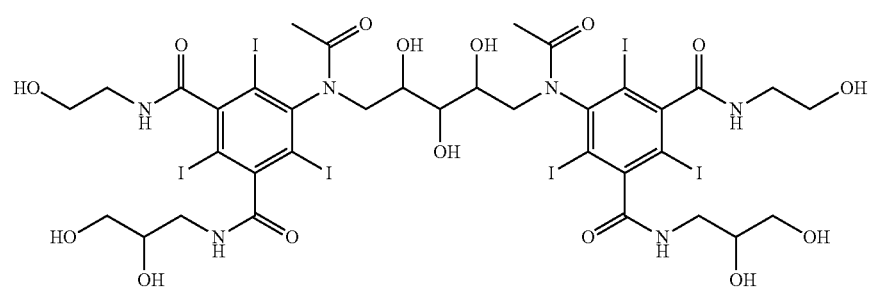
Formula (IIIo)

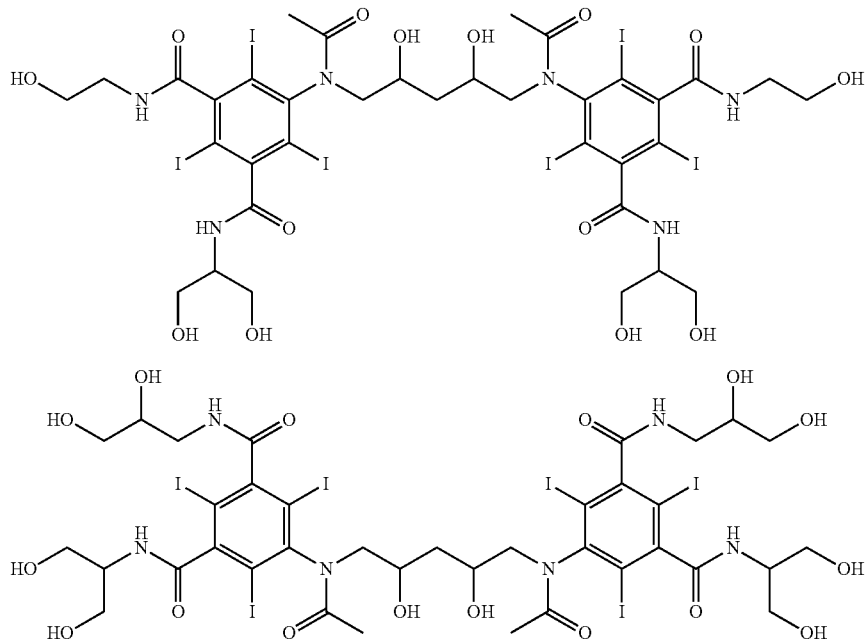

Formula (IIIp)

Formula (IIIq)

At an iodine concentration of 320 mg/ml, which is a common concentration for commercially available iodinated contrast media, the concentration of the compound of formula (I) will be approximately 0.42 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/011094 and WO 91/13636.

Compounds of formula (I) also comprises optical active isomers and may exist in several isomeric forms due to chiral carbon atoms. In addition, the compounds exhibit exo/endo isomerism due to the restricted rotation of the N—CO bond in the. acetyl functions caused by the proximity of the bulk iodine atom. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be in concentrated form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/011094 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

The contrast media containing compounds of formula (I) can be administered by injection or infusion, e.g. by intervascular administration. Alternatively, contrast media containing compounds of formula (I) may also be administered orally. For oral administration the contrast medium may be in the form of a capsule, tablet or as liquid solution.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

Preparation

The compounds of the general formula (I) can be synthesized by multistep procedures from starting materials that are either known from the state of art or that are commercially available or can readily be producted from commercially available materials. The known synthesis for the production of iodixanol (see e.g. EP 108638) can generally be adapted to produce compounds of formula (I).

General procedure for preparation of compounds of formula (I):

Compounds of formula (IV)

R—NH(CO—CH₃)   Formula (IV)

are reacted with a reactive linker group of formula (V)

Y—X—Y'   Formula (V)

wherein Y and Y' are readily eliminatable atoms or groups and X has the above meaning or a hydroxyl protected derivative thereof, or a corresponding epoxide in which one or both of the substituents Y and Y' are replaced by —O—. If required, the reaction is followed by removal of protecting groups. The groups Y and Y' may be chosen from halogen atoms, e.g. chloride, bromine or iodine, or sulphate hydrocarbylsulphonyloxy groups, e.g. alkyl- or aryl-sulphonyloxy groups such as tosyloxy or mesyloxy. The compound of formula (V) may thus be

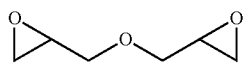

2-[(Oxiran-2-ylmethoxy)methyl]oxirane

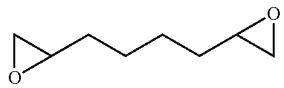

2-(4-Oxiran-2-ylbutyl)oxirane

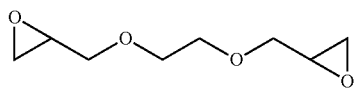 [SMILES: C(COCC1CO1)OCC1CO1]

2-{[2-(Oxiran-2-ylmethoxy)ethoxy]methyl}oxirane

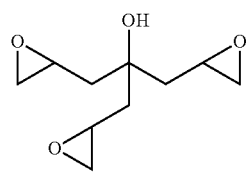 [SMILES: OC(CC1CO1)(CC1CO1)CC1CO1]

1,3-Dioxiran-2-yl-2-(oxiran-2-ylmethyl)propan-2-ol

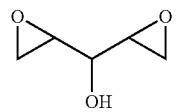

Dioxiran-2-ylmethanol

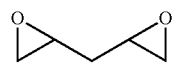

2-(Oxiran-2-ylmethyl)oxirane or any precursor that can form terminal epoxides under basic conditions like 1,5-Dichloro-pentane-2,4-diol, see Scott D. Rychnovsky, J George Griesgraber, Sam Zeller, and Donald J. Skalitzky, J. Org. Chem. 1991, 56, 5161-5169 or 2,4-Dibromo-pentane-1,5-diol, see Schreiber, Stuart L.; Goulet, Mark T.; Schulte, Gayle; J. Am. Chem. Soc.; EN; 109; 15; 1987; 4718-4720.

The hydroxyl groups present in the R groups and in the X group may, if desired, be in a hydroxyl protected form. Suitable protecting groups include acyl groups such as acetyl or, where adjacent hydroxyl groups are present, as cyclic ketal or acetal groups.

The reaction between compounds of formulas (IV) and (V) is preferably effected in the presence of an acid binding agent, for example an organic or inorganic base preferably in aqueous or alcoholic medium or mixtures thereof such as water and/or an alkanol or glycol; an alkali metal alkoxide such as sodium methoxide or an alkali metal hydroxide such as sodium and potassium hydroxide may be used as base.

Any protecting group may be removed by standard methods, for example by hydrolysis. The compounds of formula (IV) may be prepared by acetylation of the corresponding compounds having free amino groups. In this reaction, hydroxyl groups in the substituents R may also be protected by acylation.

The compounds of formula (I) may be purified in any convenient manner, e.g. by preparative chromatography or by recrystallisation.

Alternatively, the compounds of formula (I) can be prepared employing the method described in Priebe et.al. (Acta Radiol. 36 (1995), Suppl. 399, 21-31 and also by adapting other methods described for the synthesis of iodixanol in the state of art.

Preparation of Intermediates

The precursors to the compounds of formulas (IV) the tri-iodinated phenyl groups having a free amino group are commercially available or can be produced following procedures described or referred to e.g. in WO95/35122 and WO98/52911. 5-amino-2,4,6-triiodo-isophtalic acid for example is available e.g. from Aldrich and 5-amino-2,4,6-triiodo-N,N'-bis(2,3-dihydroxypropyl)-isophthalamide is commercially available e.g. from Fuji Chemical Industries, Ltd.

Examples of precursors of the compounds of formulas (IV), either commercially available or previously described in the literature include:

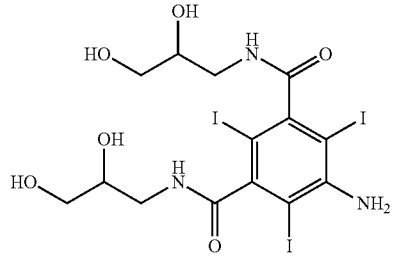 [SMILES: Nc1c(I)c(C(=O)NCC(O)CO)c(I)c(C(=O)NCC(O)CO)c1I]

5-amino-N,N'-bis(2,3-dihydroxypropyl)-2,4,6-tri-iodo-1,3benzenedicarboxamide

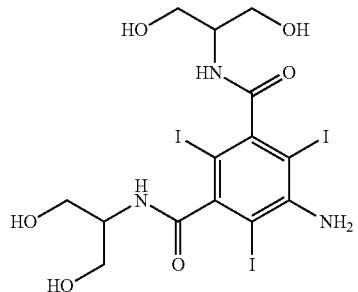 [SMILES: Nc1c(I)c(C(=O)NC(CO)CO)c(I)c(C(=O)NC(CO)CO)c1I]

5-amino-N,N'-bis[1,3-dihydroxy-2-propyl]-2,4,6-triiodo-1,3-benzenedicarboxamide (WO2002044125)

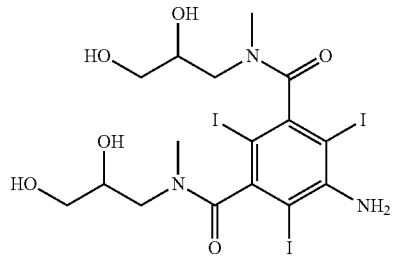 [SMILES: CN(CC(O)CO)C(=O)c1c(I)c(N)c(I)c(C(=O)N(C)CC(O)CO)c1I]

5-amino-N,N'-bis(2,3-dihydroxypropyl)-N,N'-dimethyl-2,4,6-triiodo-1,3-benzenedicarboxamide

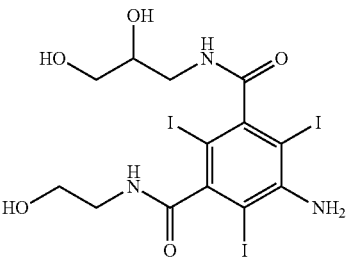 [SMILES: Nc1c(I)c(C(=O)NCCO)c(I)c(C(=O)NCC(O)CO)c1I]

5-amino-N-(2,3-dihydroxypropyl)-N'-(2-hydroxyethyl)-2,4,6-triiodo-1,3-benzenedicarboxamide (WO 8700757)

The compounds of formulas (IV) may be prepared by acylation and more specificly acetylation of the corresponding compounds having free amino groups. In this reaction, hydroxyl groups in the substituents R may also be protected by acylation.

The acylation may be effected by any convenient method, e.g. by use of activated acetic acid such as acetic anhydride or mixed anhydrides which can prepared by a variety of methods described in the literature, see e.g. K. M. R. Pillai, G. Diamantidis, L. Duncan and R. S. Ranganathan J. Org. Chem. 1994, 59, 1344-1350.

EXPERIMENTAL

TFA—Trifluoroacetic acid

Example 1

5,5'-(3,3'-oxybis(2-hydroxypropane-3,1-diyl)bis(acetylazanediyl)bis($N^1$,$N^3$-bis(2,3-dihydroxypropyl)-2,4,6-triiodoisophthalamide)

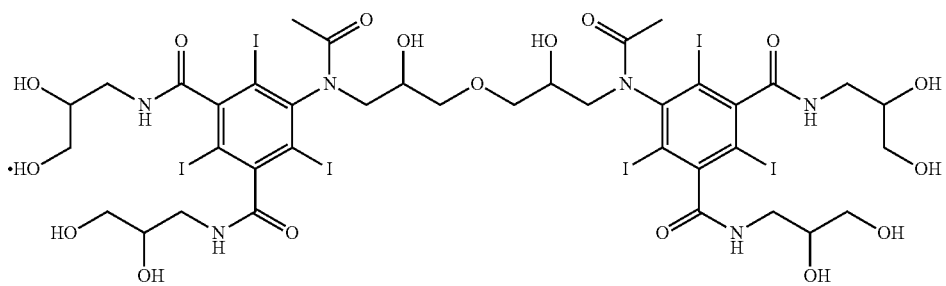

To a stirred solution of water/methanol (14.7 ml, 7.3 ml) and potassium hydroxide (1.46 g, 26.1 mmol) at 40° C. was added 5-acetylamino-N,N'-bis-(2,3-dihydroxypropyl)-2,4,6-triiodo isophthalamide (15.0 g, 20.1 mmol). To the clear solution was then added boric acid (0.86 g, 13.9 mmol). The mixture was cooled to room temperature and pH adjusted to 12.6. 2-[(oxiran-2-ylmethoxy)methyl]oxirane (0.90 g, 6.9 mmol) was added. The pH of the solution was adjusted to the interval 12.6-13. The reaction was left over night. To the solution was added HCl (18%) to pH 4. Salts were removed by treatment with ion exchanger AMB200C and IRA67. The solution was filtered from the resin and evaporated. The crude product was lyophilized and obtained in 7.9 g. An aliquot of the crude material was purified by preparative HPLC (column Phenomenex Luna C18(2) 10 μm 250×50.0 mm, solvents: A=water and B=acetonitrile; gradient 02-08% B over 60 min; flow 50.0 ml/min, UV detection at 214 nm and 254 nm). The product was obtained in 389 mg after lyophilisation. Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave two peaks at 7.16 and 7.30 minutes with m/z 1624.7 (MH$^+$) corresponding to the structure.

Example 2

5,5'-(3,3'-oxybis(2-hydroxypropane-3,1-diyl))bis(acetylazanediyl)bis($N^1,N^1,N^3,N^3$-tetrakis(2-hydroxyethyl)-2,4,6-triiodoisophthalamide)

2-ylmethoxy)methyl]oxirane (0.29 g, 2.26 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying, 806 mg of the title product (37%) was obtained.

Analysis by LC-MS (column Agilent Zorbax SB-Aq 3.5 μm 3.0×100 mm, solvents: A=water/0.1% TFA and B=acetonitrile/0.1% TFA; gradient 0-20% B over 10 min; flow 0.3 ml/min, UV detection at 214 and 254 nm, ESI-MS) gave two peaks centered at 7.5 minutes with m/z 1681.0 (MH$^+$) corresponding to the structure.

$^1$H NMR, 500 MHz (DMSO-d6, 25° C.): 1.75-2.2 ppm (m, 6H), 3.00-5.8 ppm (m, 58H).

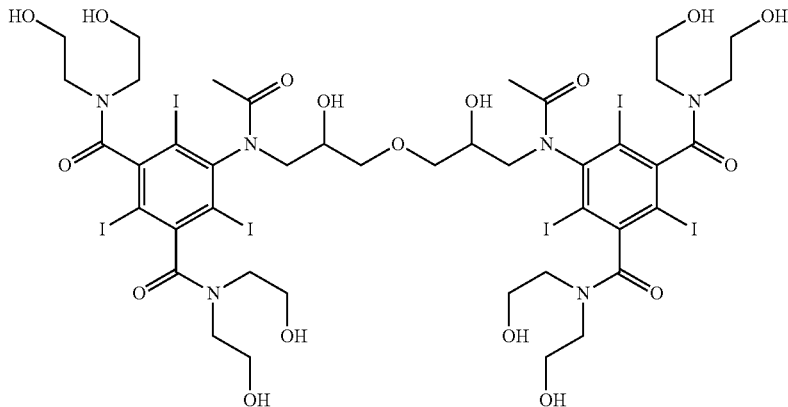 [SMILES: CC(=O)N(CC(O)COCC(O)CN(C(C)=O)c1c(I)c(C(=O)N(CCO)CCO)c(I)c(C(=O)N(CCO)CCO)c1I)c1c(I)c(C(=O)N(CCO)CCO)c(I)c(C(=O)N(CCO)CCO)c1I]

5-Acetylamino-N,N,N',N'-tetrakis-(2-hydroxy-ethyl)-2,4,6-triiodo-isophthalamide (5 g, 6.45 mmol) was added to a stirring solution of potassium hydroxide in a mixture of methanol/water (50/50). To the clear and slightly yellow solution which was obtained was added boric acid (0.35 g, 5.6 mmol). The pH was continuously maintained at pH 12.6 by addition of potassium hydroxide (10 M) and then 2-[(oxiran- Example 3

5,5'-(3,3'-oxybis(2-hydroxypropane-3,1-diyl))bis(acetylazanediyl)bis($N^1,N^3$-bis(2,3-dihydroxypropyl)-2,4,6-triiodo-$N^1,N^3$-dimethylisophthalamide)

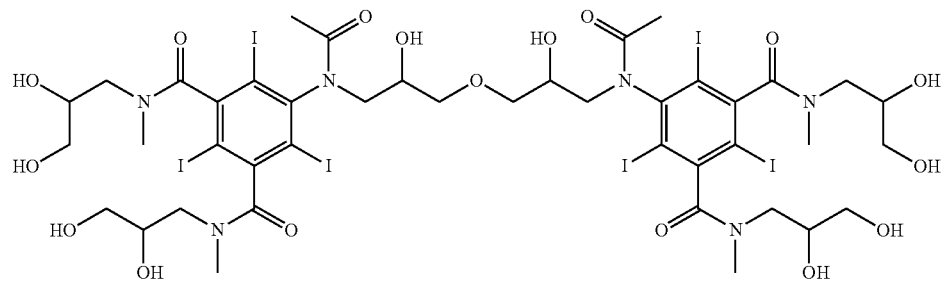 [SMILES: CC(=O)N(CC(O)COCC(O)CN(C(C)=O)c1c(I)c(C(=O)N(C)CC(O)CO)c(I)c(C(=O)N(C)CC(O)CO)c1I)c1c(I)c(C(=O)N(C)CC(O)CO)c(I)c(C(=O)N(C)CC(O)CO)c1I]

To a stirred solution of water/methanol (1.97 ml, 0.98 ml) and potassium hydroxide (0.17 g, 3.1 mmol) at 40° C. was added 5-acetylamino-N,N'-bis-(2,3-dihydroxypropyl)-2,4,6-triiodo-N,N'-dimethyl isophthalamide (2.0 g, 2.58 mmol). To the clear solution was then added boric acid (0.11 g, 1.78 mmol). The mixture was cooled to room temperature and pH adjusted to 12.6. 2-[(oxiran-2-ylmethoxy)methyl]oxirane (0.120 g, 0.92 mmol) was added. The pH of the solution was adjusted to the interval 12.6-13. The reaction was left over night. Analysis by LC-MS showed a small amount of the wanted dimer. A new portion of diglycidyl ether (33.8 mg, 0.26 mmol) was added and the reaction left over night. New analysis showed improvement. Another portion of the linker (same amount) was added and the reaction was left over night. To the solution was then added HCl (18%) to pH 4. Salts were removed by treatment with ion exchanger AMB200C and IRA67. The solution was filtered from the resin and evaporated. The crude product was lyophilized. An aliquot of the material was purified by preparative HPLC (column Phenomenex Luna C18(2) 10 μm 250×50.0 mm, solvents: A=water and B=acetonitrile; gradient 02-10% B over 60 min; flow 50.0 ml/min, UV detection at 214 nm and 254 nm), the product was obtained in 237 mg after lyophilisation.

Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a split peak at 8.13 and 8.28 minutes with m/z 1680.4 (MH$^+$) corresponding to the structure.

Example 4

5,5'-(2,7-dihydroxyoctane-1,8-diyl)bis(acetylazanediyl)bis(N$^1$,N$^1$,N$^3$, N$^3$-tetrakis(2-hydroxyethyl)-2,4,6-triiodoisophthalamide)

5-Acetylamino-N,N,N',N'-tetrakis-(2-hydroxy-ethyl)-2,4,6-triiodo-isophthalamide (5 g, 6.45 mmol) was added to a stirring solution of potassium hydroxide (0.54 g, 6.5 mmol) in a mixture of methanol (3.5 ml) and water (3.5 ml). To the clear and slightly yellow solution which was obtained was added boric acid (0.35 g, 5.6 mmol). The pH was continuously maintained at pH 12.6 by addition of potassium hydroxide (10 M) and then 2-(4-oxiran-2-ylbutyl)oxirane (0.32 g, 2.24 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying, 869 mg of the title product (47%) was obtained.

Analysis by LC-MS (column Agilent Zorbax SB-Aq 3.5 μm 3.0×100 mm, solvents: A=water/0.1% TFA and B=acetonitrile/0.1% TFA; gradient 0-40% B over 5 min; flow 0.3 ml/min, UV detection at 214 and 254 nm, ESI-MS) gave one broad peak centered at 2.59 minutes with m/z 1692.5 (MH$^+$) corresponding to the structure.

$^1$H NMR, 500 MHz (DMSO-d6, 25° C.): 1.30-1.6 ppm (m, 8H), 1.7-2.2 (m, 6H), 2.95-4.8 ppm (m, 48H).

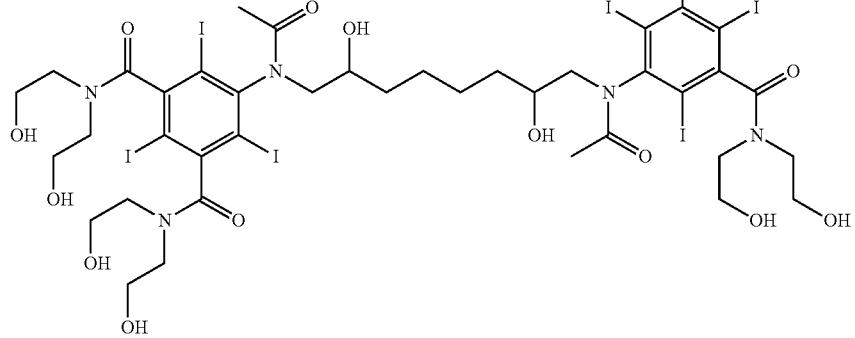

Example 5

5,5'-(5,12-dihydroxy-2,15-dioxo-7,10-dioxa-3,14-diazahexadecane-3,14-diyl)bis($N^1,N^1,N^3,N^3$-tetrakis(2-hydroxyethyl)-2,4,6-triiodoisophthalamide)

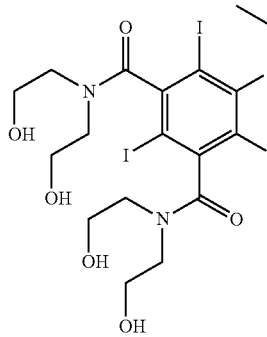

5-Acetylamino-N,N,N',N'-tetrakis-(2-hydroxy-ethyl)-2,4,6-triiodo-isophthalamide (5 g, 6.45 mmol) was added to a stirring solution of potassium hydroxide (0.54 g, 6.5 mmol) in a mixture of methanol (3.5 ml) and water (3.5 ml). To the clear and slightly yellow solution which was obtained was added boric acid (0.35 g, 5.6 mmol). The pH was continuously maintained at pH 12.6 by addition of potassium hydroxide (10 M) and then 2-{[2-(oxiran-2-ylmethoxy)ethoxy]methyl}oxirane (0.39 g, 2.24 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 µm 250×50.0 mm, solvents: A=water and B=acetonitrile; gradient 0-10% B over 60 min; flow 50.0 ml/min, UV detection at 214 nm and 254 nm). After freeze-drying, 377 mg of the title product (21%) was obtained.

Analysis by LC-MS (column Agilent Zorbax SB-Aq 3.5 µm 3.0×100 mm, solvents: A=water/0.1% TFA and B=acetonitrile/0.1% TFA; gradient 0-40% B over 5 min; flow 0.3 ml/min, UV detection at 214 and 254 nm, ESI-MS) gave one broad peak centered at 2.59 minutes with m/z 1724.6 (MH$^+$) corresponding to the structure.

$^1$H NMR, 500 MHz (DMSO-d6, 25° C.): 1.75-2.21 ppm (m, 6H), 3.05-4.95 ppm (m, 56H).

Example 6

5-(N-((4-(3-(N-(3,5-bis(bis(2-hydroxyethyl)carbamoyl)-2,4,6-triiodophenyl)acetamido)-2-hydroxypropyl)-4-hydroxy-6-(hydroxymethyl)tetrahydro-2H-pyran-2-yl)methyl)acetamido)-$N^1,N^1,N^3,N^3$-tetrakis(2-hydroxyethyl)-2,4,6-triiodoisophthalamide

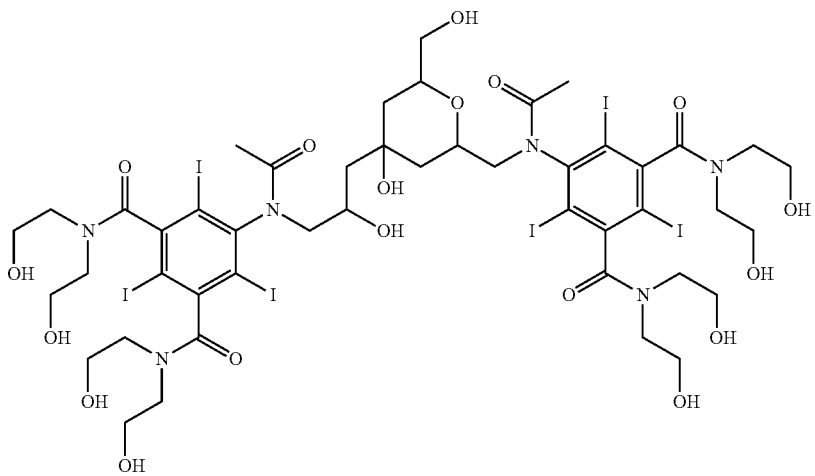 [SMILES: CC(=O)N(CC(O)CC1(O)CC(CO)OC(CN(C(C)=O)c2c(I)c(C(=O)N(CCO)CCO)c(I)c(C(=O)N(CCO)CCO)c2I)C1)c1c(I)c(C(=O)N(CCO)CCO)c(I)c(C(=O)N(CCO)CCO)c1I]

5-Acetylamino-N,N,N',N'-tetrakis-(2-hydroxy-ethyl)-2,4,6-triiodo-isophthalamide (5 g, 6.45 mmol) was added to a stirring solution of potassium hydroxide (0.57 g, 10.1 mmol) in a mixture of methanol (3.5 ml) and water (3.5 ml). To the clear and slightly yellow solution which was obtained was added boric acid (0.35 g, 5.6 mmol). The pH was continuously maintained at pH 12.6 by addition of potassium hydroxide (10 M) and then 1,3-bis-oxiranyl-2-oxiranylmethyl-propan-2-ol (0.22 g, 1.09 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying, 290 mg of the title product was obtained.

Analysis by LC-MS (column Agilent Zorbax SB-Aq 3.5 μm 3.0×100 mm, solvents: A=water/0.1% TFA and B=acetonitrile/0.1% TFA; gradient 0-40% B over 5 min; flow 0.3 ml/min, UV detection at 214 and 254 nm, ESI-MS) gave one broad peak centered at 2.36 minutes with m/z 1750.5 (MH$^+$) corresponding to the structure.

Example 7

5,5'-(2,7-dihydroxyoctane-1,8-diyl)bis(acetylazanediyl)bis(N$^1$,N$^3$-bis(2,3-dihydroxypropyl)-2,4,6-triiodoisophthalamide)

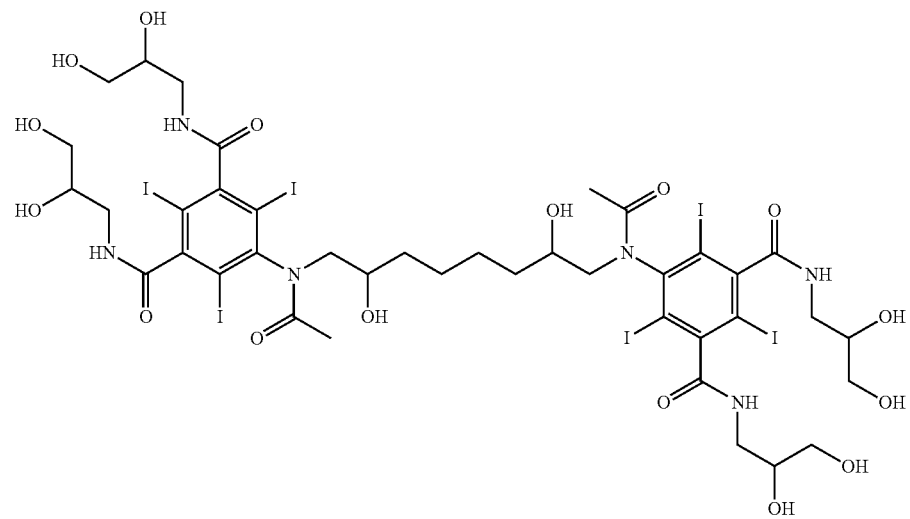 [SMILES: CC(=O)N(CC(O)CCCCC(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water/methanol (4.9 ml, 2.5 ml) and potassium hydroxide (0.49 g, 8.7 mmol) at 40° C. was added 5-acetylamino-N,N'-bis-(2,3-dihydroxypropyl)-2,4,6-triiodo isophthalamide (5.0 g, 6.7 mmol). To the clear solution was then added boric acid (0.29 g, 4.6 mmol). The mixture was cooled to room temperature and pH adjusted to 12.6. 2-(4-oxiran-2-ylbutyl)oxirane (0.327 g, 2.3 mmol) was added. The pH of the solution was adjusted to the interval 12.6-13. The reaction was left over weekend. To the solution was added HCl (18%) to pH 4. Salts were removed by treatment with ion exchanger AMB200C and IRA67. The solution was filtered from the resin and evaporated. An aliquot of the crude material was purified by preparative HPLC (column Phenomenex Luna C18(2) 10 μm 250×50.0 mm, solvents: A=water and B=acetonitrile; gradient 07-13% B over 60 min; flow 50.0 ml/min, UV detection at 214 nm and 254 nm). The product was obtained in 639 mg after lyophilisation. Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave two isomeric peaks eluting between 12.50-12.85 minutes with m/z 1636.6 (MH$^+$) corresponding to the structure.

Example 8

5,5'-(2,7-dihydroxyoctane-1,8-diyl)bis(acetylazanediyl)bis(N¹,N³-bis(2,3-dihydroxypropyl)-2,4,6-triiodo-N¹,N³-dimethylisophthalamide)

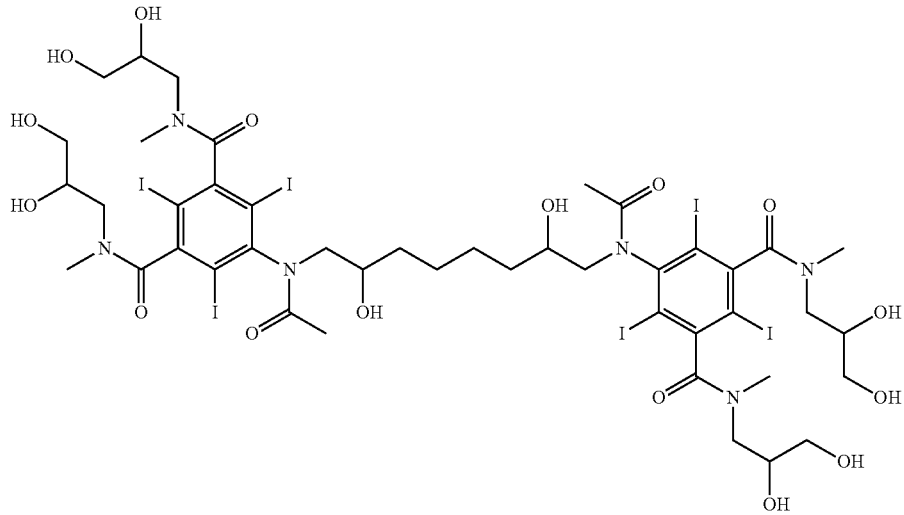 [SMILES: CC(=O)N(CC(O)CCCCC(O)CN(C(C)=O)c1c(I)c(C(=O)N(C)CC(O)CO)c(I)c(C(=O)N(C)CC(O)CO)c1I)c1c(I)c(C(=O)N(C)CC(O)CO)c(I)c(C(=O)N(C)CC(O)CO)c1I]

To a stirred solution of water/methanol (4.9 ml, 2.5 ml) and potassium hydroxide (0.47 g, 8.4 mmol) at 40° C. was added 5-acetylamino-N,N'-bis-(2,3-dihydroxypropyl)-2,4,6-triiodo-N,N'-dimethyl isophthalamide (5.0 g, 6.5 mmol). To the clear solution was then added boric acid (0.28 g, 4.5 mmol). The mixture was cooled to room temperature and pH adjusted to 12.6. 2-(4-oxiran-2-ylbutyl)oxirane (0.315 g, 2.22 mmol) was added. The pH of the solution was adjusted to the interval 12.6-13. The reaction was left over weekend. To the solution was added HCl (18%) to pH 4. Salts were removed by treatment with ion exchanger AMB200C and IRA67. The solution was filtered from the resin and evaporated. An aliquot of the crude material was purified by preparative HPLC (column Phenomenex Luna C18(2) 10 μm 250×50.0 mm, solvents: A=water and B=acetonitrile; gradient 10-18% B over 60 min; flow 50.0 ml/min, UV detection at 214 nm and 254 nm), the product was obtained in 393 mg after lyophilisation. Analysis by LC-MS (column Agilent Zorbax SB-Aq 3.5 μm 3.0×100 mm, solvents: A=water/0.1% formic acid and B=acetonitrile/ 0.1% formic acid; gradient 0-30% B over 20 min; flow 0.3 ml/min, UV detection at 214 and 254 nm, ESI-MS) gave one broad peak centred at 14.77 minutes with m/z 1692.6 (MH⁺) corresponding to the structure.

Example 9

5,5'-(5,12-dihydroxy-2,15-dioxo-7,10-dioxa-3,14-diazahexadecane-3,14-diyl)bis(N¹,N³-bis(2,3-dihydroxypropyl)-2,4,6-triiodoisophthalamide)

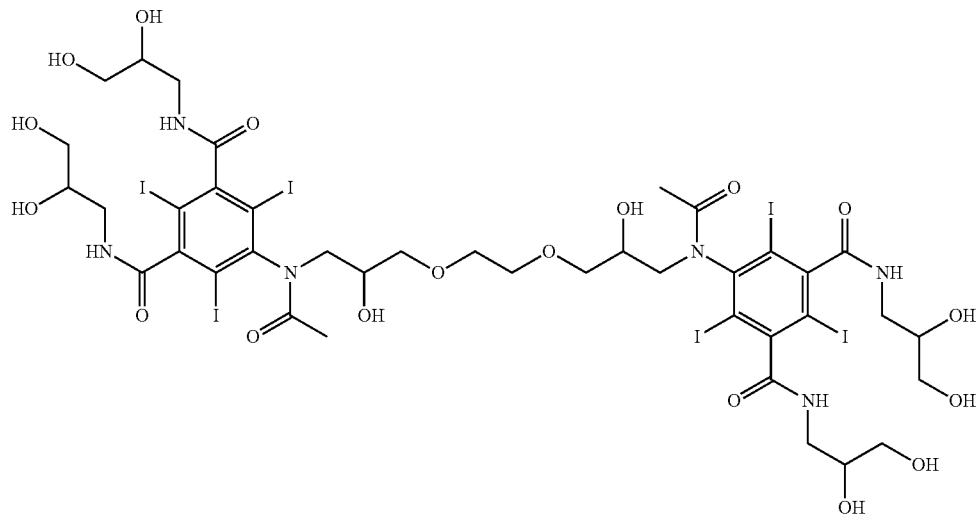 [SMILES: CC(=O)N(CC(O)COCCOCC(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water/methanol (4.9 ml, 2.5 ml) and potassium hydroxide (0.49 g, 8.7 mmol) at 40° C. was added 5-acetylamino-N,N'-bis-(2,3-dihydroxypropyl)-2,4,6-triiodo isophthalamide (5.0 g, 6.7 mmol). To the clear solution was then added boric acid (0.29 g, 4.6 mmol). The mixture was cooled to room temperature and pH adjusted to 12.6. 2-{[2-(oxiran-2-ylmethoxy)ethoxy]methyl}-oxirane (0.40 g, 2.3 mmol) was added. The pH of the solution was adjusted to the interval 12.6-13. The reaction was left over weekend. To the solution was added HCl (18%) to pH 4. Salts were removed by treatment with ion exchanger AMB200C and IRA67. The solution was filtered from the resin and evaporated. The product was purified by preparative HPLC (column Phenomenex Luna C18(2) 10 μm 250×50.0 mm, solvents: A=water and B=acetonitrile; gradient 05-10% B over 60 min; flow 50.0 ml/min, UV detection at 214 nm and 254 nm), and obtained in 268 mg after lyophilisation, 7% yield. Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave three isomeric peaks centred at 11.7 minutes with m/z 1668.5 (MH$^+$) corresponding to the structure.

Example 10

5,5'-(5,12-dihydroxy-2,15-dioxo-7,10-dioxa-3,14-diazahexadecane-3,14-diyl)bis(N$^1$,N$^3$-bis(2,3-dihydroxypropyl)-2,4,6-triiodo-N$^1$,N$^3$-dimethylisophthalamide)

To a stirred solution of water/methanol (4.9 ml, 2.5 ml) and potassium hydroxide (0.47 g, 8.4 mmol) at 40° C. was added 5-acetylamino-N,N'-bis-(2,3-dihydroxypropyl)-2,4,6-triiodo-N,N'-dimethyl isophthalamide (5.0 g, 6.5 mmol). To the clear solution was then added boric acid (0.28 g, 4.5 mmol). The mixture was cooled to room temperature and pH adjusted to 12.6. 2-{[2-(oxiran-2-ylmethoxy)-ethoxy]methyl}oxirane (0.382 g, 2.22 mmol) was added. The pH of the solution was adjusted to the interval 12.6-13. The reaction was left over weekend. To the solution was added HCl (18%) to pH 4. Salts were removed by treatment with ion exchanger AMB200C and IRA67. The solution was filtered from the resin and evaporated. The product was purified by preparative HPLC (column YMC amino 21.2×250 mm, solvents: A=water and B=acetonitrile; gradient 85-65% B over 25 min; flow 25.0 ml/min, UV detection at 214 nm and 254 nm), and obtained in 180 mg after lyophilisation, 5% yield. Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave one broad peak centred at 9.6 minutes with m/z 1724.6 (MH$^+$) corresponding to the structure.

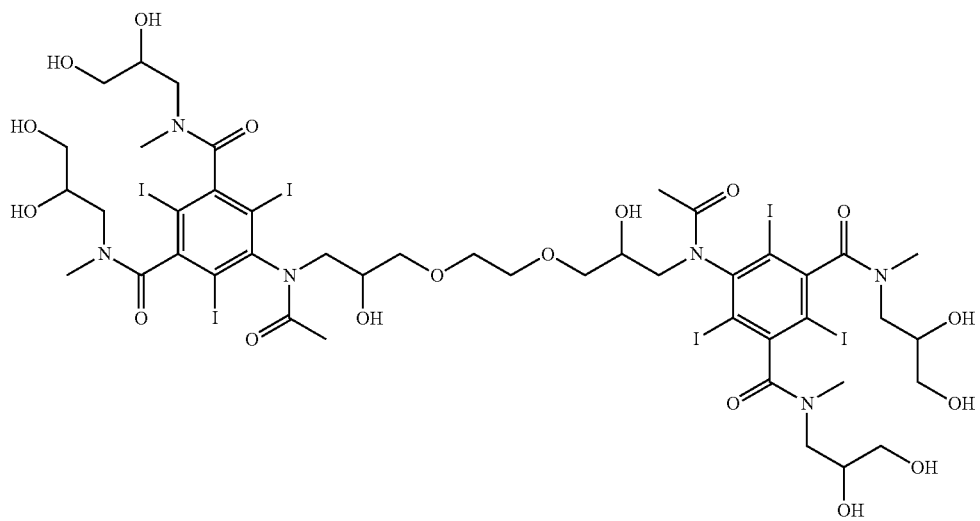 [SMILES: CC(=O)N(CC(O)COCCOCC(O)CN(C(C)=O)c1c(I)c(C(=O)N(C)CC(O)CO)c(I)c(C(=O)N(C)CC(O)CO)c1I)c1c(I)c(C(=O)N(C)CC(O)CO)c(I)c(C(=O)N(C)CC(O)CO)c1I]

Example 11

5,5'-(2,3,4-trihydroxypentane-1,5-diyl)bis(acetylazanediyl)bis(N¹,N¹,N³,N³-tetrakis(2-hydroxyethyl)-2,4,6-triiodoisophthalamide)

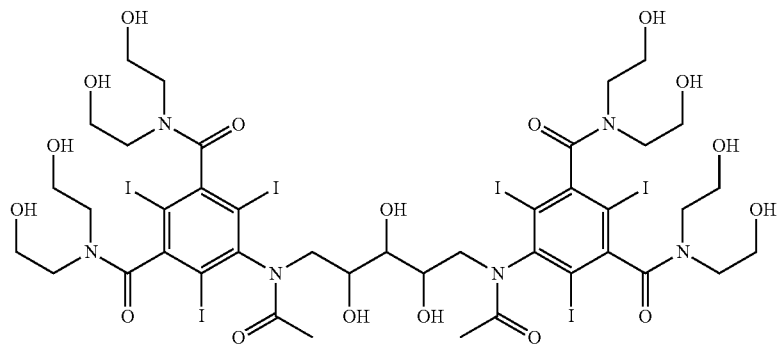 [SMILES: CC(=O)N(CC(O)C(O)C(O)CN(C(C)=O)c1c(I)c(C(=O)N(CCO)CCO)c(I)c(C(=O)N(CCO)CCO)c1I)c1c(I)c(C(=O)N(CCO)CCO)c(I)c(C(=O)N(CCO)CCO)c1I]

5-Acetylamino-N,N,N',N'-tetrakis-(2-hydroxy-ethyl)-2,4,6-triiodo-isophthalamide (5 g, 6.50 mmol) was added to a stirring solution of potassium hydroxide (0.52 g, 9.3 mmol) in a mixture of methanol (3.5 ml) and water (3.5 ml). To the clear and slightly yellow solution which was obtained was added boric acid (0.35 g, 5.6 mmol). The pH was continuously maintained at pH 12.6 by addition of potassium hydroxide (10 M) and then dioxiran-2-ylmethanol (0.26 g, 2.26 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 µm 250×50.0 mm, solvents: A=water and B=acetonitrile; gradient 0-10% B over 60 min; flow 50.0 ml/min, UV detection at 214 nm and 254 nm). After freeze-drying, 300 mg of the title product (8%) was obtained.

Analysis by LC-MS (column Agilent Zorbax SB-Aq 3.5 µm 3.0×100 mm, solvents: A=water/0.1% TFA and B=acetonitrile/0.1% TFA; gradient 05-20% B over 5 min; flow 0.3 ml/min, UV detection at 214 and 254 nm, ESI-MS) gave multiple peaks centered at 2.64 minutes with m/z 1666.7 (MH⁺) corresponding to the structure.

¹H NMR, 500 MHz (DMSO-d6, 25° C.): 1.70-2.24 ppm (m, 6H), 3.05-4.95 ppm (m, 50H).

Example 12

5,5'-(2,3,4-trihydroxypentane-1,5-diyl)bis(acetylazanediyl)bis(N¹,N³-bis(2,3-dihydroxypropyl)-2,4,6-triiodoisophthalamide)

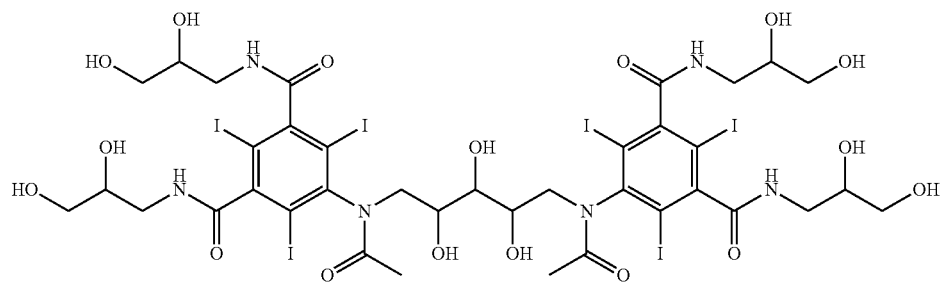 [SMILES: CC(=O)N(CC(O)C(O)C(O)CN(C(C)=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

To a stirred solution of water/methanol (4.9 ml, 2.5 ml) and potassium hydroxide (0.49 g, 8.7 mmol) at room temperature was added 5-acetylamino-N,N'-bis-(2,3-dihydroxypropyl)-2,4,6-triiodo isophthalamide (5.0 g, 6.7 mmol). To the clear solution was then added boric acid (0.29 g, 4.6 mmol). The pH was measured and adjusted to 12.6. Dioxiran-2-ylmethanol (0.363 g, 2.35 mmol) was added. The pH of the solution was adjusted to the interval 12.6-13. The mixture was allowed to react for 7 days. To the solution was added HCl (18%) to pH 4. Salts were removed by treatment with ion exchanger AMB200C and IRA67. The solution was filtered from the resin and evaporated. The product was purified by preparative HPLC (column Phenomenex Luna C18(2) 10 µm 250×50.0 mm, solvents: A=water and B=acetonitrile; gradient 03-10% B over 60 min; flow 50.0 ml/min, UV detection at 214 nm and 254 nm) and obtained in 100 mg after lyophilisation, 3% yield. Analysis by LC-MS (column Agilent Zorbax SB-Aq 3.5 µm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave three isomeric peaks centred at 9.13 minutes with m/z 1610.5 (MH⁺) corresponding to the structure.

Example 13

5,5'-(2,3,4-trihydroxypentane-1,5-diyl)bis(acetylazanediyl)bis($N^1$,$N^3$-bis(2,3-dihydroxypropyl)-2,4,6-triiodoisophthalamide)

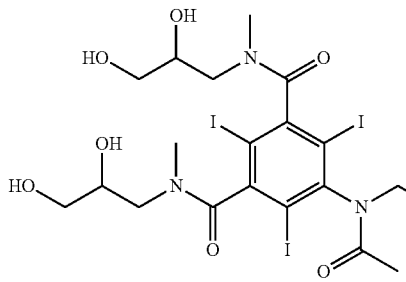

To a stirred solution of water/methanol (4.9 ml, 2.5 ml) and potassium hydroxide (0.47 g, 8.4 mmol) at 40° C. was added 5-acetylamino-N,N'-bis-(2,3-dihydroxypropyl)-2,4,6-triiodo-N,N'-dimethyl isophthalamide (5.0 g, 6.5 mmol). To the clear solution was then added boric acid (0.28 g, 4.5 mmol). The pH was measured and adjusted to 12.6. Dioxiran-2-ylmethanol (0.353 g, 2.28 mmol) was added. The pH of the solution was adjusted to the interval 12.6-13. The mixture was allowed to react for 7 days. To the solution was added HCl (18%) to pH 4. Salts were removed by treatment with ion exchanger AMB200C and IRA67. The solution was filtered from the resin and evaporated. The product was purified by preparative HPLC (column Phenomenex Luna C18(2) 10 μm 250×50.0 mm, solvents: A=water and B=acetonitrile; gradient 0-20% B over 60 min; flow 50.0 ml/min, UV detection at 214 nm and 254 nm) and obtained in 588 mg after lyophilisation, 15% yield. Analysis by LC-MS (column Agilent Zorbax SB-Aq 3.5 μm 3.0×100 mm, solvents: A=water/0.1% formic acid and B=acetonitrile/0.1% formic acid; gradient 0-30% B over 20 min; flow 0.3 ml/min, UV detection at 214 and 254 nm, ESI-MS) gave a broad multiplet centred at 11.88 minutes with m/z 1666.6 (MH$^+$) corresponding to the structure.

Example 14

5,5'-(2,4-dihydroxypentane-1,5-diyl)bis(acetylazanediyl)bis($N^1$,$N^1$,$N^3$,$N^3$-tetrakis(2-hydroxyethyl)-2,4,6-thiodoisophthalamide)

5-Acetylamino-N,N,N',N'-tetrakis-(2-hydroxy-ethyl)-2,4,6-triiodo-isophthalamide (5 g, 6.50 mmol) was added to a stirring solution of potassium hydroxide (0.52 g, 9.3 mmol) in a mixture of methanol (3.5 ml) and water (3.5 ml). To the clear and slightly yellow solution which was obtained was added boric acid (0.35 g, 5.6 mmol). The pH was continuously maintained at pH 12.6 by addition of potassium hydroxide (10 M) and then 2-(oxiran-2-ylmethyl)oxirane (0.23 g, 2.26 mmol) was added. The pH of the solution was continuously maintained within the interval 12 and 13 by addition of solid boric acid for 5 hours. And the mixture stirred at ambient temperature overnight (20 hours). LC-MS investigation showed formation of the expected product. Using 18.5 M HCl (50%), the mixture was made acidic, pH 3.5-4.5 and stirred overnight again. Precipitation of unreacted monomer had occurred and removed by filtration of the mixture (funnel sinter 3) and the filter cake washed with water (2×5 ml). The filtrate was then treated with ion exchangers (AMB200C, 9 ml) and (IRA-67, 10 ml). The resins were removed by filtration and rinsed with water and the combined aqueous volume was reduced in vacuo. The crude product was purified by preparative HPLC (column Phenomenex Luna C18 (2) 10 μm 250×50.0 mm, solvents: A=water and B=acetonitrile; gradient 0-10% B over 60 min; flow 50.0 ml/min, UV detection at 214 nm and 254 nm). After freeze-drying, 500 mg of the title product (16%) was obtained.

Analysis by LC-MS (column Agilent Zorbax SB-Aq 3.5 μm 3.0×100 mm, solvents: A=water/0.1% TFA and B=acetonitrile/0.1% TFA; gradient 05-20% B over 5 min; flow 0.3 ml/min, UV detection at 214 and 254 nm, ESI-MS) gave multiple peaks centered at 2.64 minutes with m/z 1650.6 (MH$^+$) corresponding to the structure.

$^1$H NMR, 500 MHz (DMSO-d6, 25° C.): 1.45-1.6 ppm (m, 1H), 1.7-1.8 (m, 6H), 2.20-4.8 ppm (m, 49H).

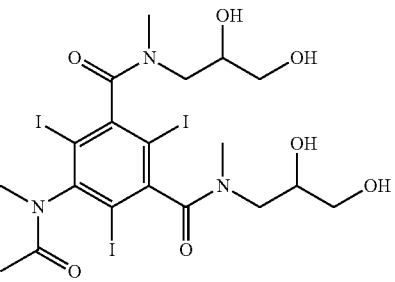

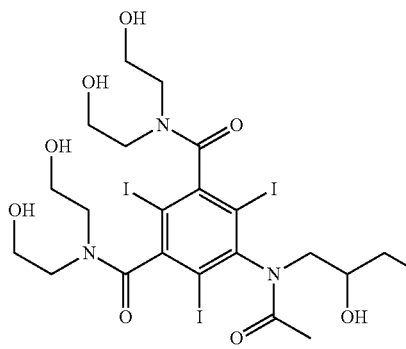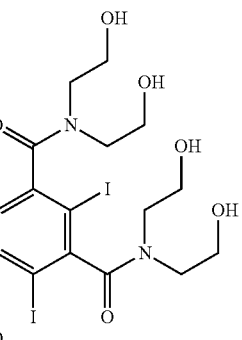

Example 15

5,5'-(2,3,4-trihydroxypentane-1,5-diyl)bis(acetylazanediyl)bis($N^1$-(2,3-dihydroxypropyl)-$N^3$-(2-hydroxyethyl)-2,4,6-triiodoisophthalamide)

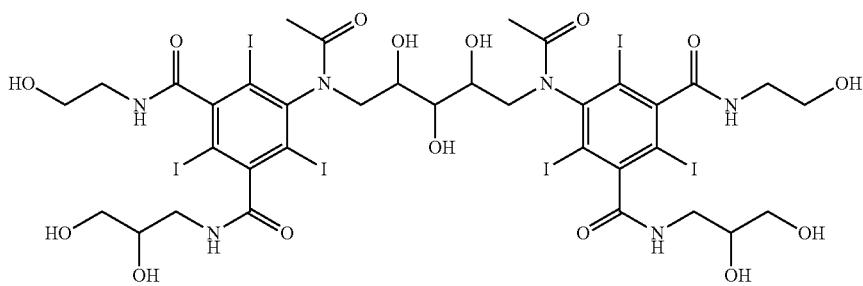 [SMILES: CC(=O)N(CC(O)C(O)C(O)CN(C(C)=O)c1c(I)c(C(=O)NCCO)c(I)c(C(=O)NCC(O)CO)c1I)c1c(I)c(C(=O)NCCO)c(I)c(C(=O)NCC(O)CO)c1I]

To a stirring solution of water (2 ml), methanol (2 ml) and potassium hydroxide (0, 34 g, 6.1 mmol) was added 5-acetylamino-N-(2,3-dihydroxy-propyl)-N'-(2-hydroxy-ethyl)-2,4,6-triiodo-isophthalamide (3.0 g, 4.2 mmol).

To the clear and slightly yellow solution which was obtained was then added boric acid (0.23 g, 3.7 mmol). The pH was continuously maintained at pH 12.6 by addition of potassium hydroxide (10 M) and then dioxiran-2-ylmethanol (0.17 g, 1.46 mmol) was added. The pH of the solution was continuously maintained within the interval 12 and 13 by addition of solid boric acid for 5 hours. And the mixture stirred at ambient temperature overnight (20 hours). Using 18.5 M HCl (50%), the mixture was made acidic to pH 3.5-4.5 and stirred overnight again and then treated with ion exchangers (AMB200C, 6 ml) and (IRA-67, 6 ml). The resins were removed by filtration and rinsed with water and the combined aqueous volume was reduced in vacuo. The crude product was purified by preparative HPLC (column Phenomenex Luna C18 (2) 10 µm 250×50.0 mm, solvents: A=water and B=acetonitrile; gradient 0-10% B over 60 min; flow 50.0 ml/min, UV detection at 214 nm and 254 nm). After freeze-drying, 420 mg of the title product (15%) was obtained.

Analysis by LC-MS (column Agilent Zorbax SB-Aq 3.5 µm 3.0×100 mm, solvents: A=water/0.1% TFA and B=acetonitrile/0.1% TFA; gradient 0-20% B over 10 min; flow 0.3 ml/min, UV detection at 214 and 254 nm, ESI-MS) gave two peaks centered at 7.5 minutes with m/z 1550.7 ($MH^+$) corresponding to the structure.

$^1$H NMR, 500 MHz (DMSO-d6, 25° C.): 1.75-2.2 ppm (m, 6H), 3.20-4.60 ppm (m, 34H), 8.0-8.6 (m, 4H)

Example 16

5,5'-(2,4-dihydroxypentane-1,5-diyl)bis(acetylazanediyl)bis($N^1$-(1,3-dihydroxypropan-2-yl)-$N^3$-(2-hydroxyethyl)-2,4,6-triiodoisophthalamide)

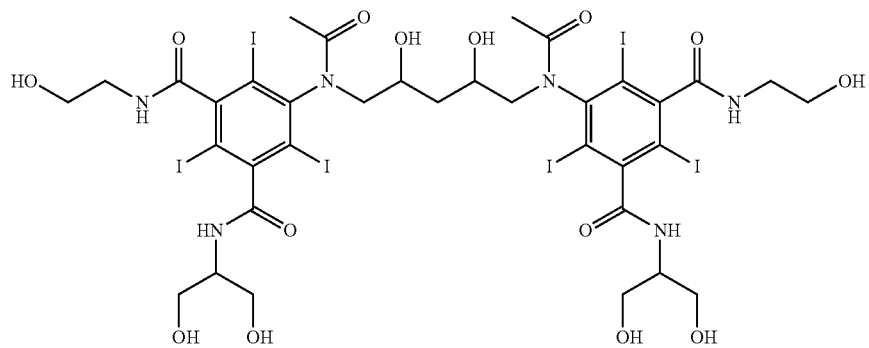 [SMILES: CC(=O)N(CC(O)CC(O)CN(C(C)=O)c1c(I)c(C(=O)NCCO)c(I)c(C(=O)NC(CO)CO)c1I)c1c(I)c(C(=O)NCCO)c(I)c(C(=O)NC(CO)CO)c1I]

To a stirring solution of water (1 ml), methanol (1 ml) and potassium hydroxide (0.17 g, 3.00 mmol) was added 5-acetylamino-N-(2-hydroxy-ethyl)-N'-(2-hydroxy-1-hydroxymethyl-ethyl)-2,4,6-triiodo-isophthalamide (1.5 g, 2.09 mmol).

To the clear and slightly yellow solution which was obtained was then added boric acid (0.11 g, 1.8 mmol). The pH was continuously maintained at pH 12.6 by addition of potassium hydroxide (10 M) and then 2-(oxiran-2-ylmethyl)oxirane (0.082 g, 0.74 mmol) was added. The pH of the solution was continuously maintained within the interval 12 and 13 by addition of solid boric acid for 5 hours. And the mixture stirred at ambient temperature overnight (20 hours). Using 18.5 M HCl (50%), the mixture was made acidic to pH 3.5-4.5 and stirred overnight again and then treated with ion exchangers (AMB200C, 2 ml) and (IRA-67, 3 ml). The resins were removed by filtration and rinsed with water and the combined aqueous volume was reduced in vacuo. The crude product was purified by preparative HPLC (column Phenomenex Luna C18 (2) 10 µm 250×50.0 mm, solvents: A=water and B=acetonitrile; gradient 0-10% B over 60 min; flow 50.0 ml/min, UV detection at 214 nm and 254 nm). After freeze-drying, 470 mg of the title product (30%) was obtained. Analysis by LC-MS (column Agilent Zorbax SB-Aq 3.5 μm 3.0×100 mm, solvents: A=water/0.1% TFA and B=acetonitrile/0.1% TFA; gradient 0-20% B over 10 min; flow 0.3 ml/min, UV detection at 214 and 254 nm, ESI-MS) gave two peaks centered at 7.5 minutes with m/z 1535.8 (MH$^+$) corresponding to the structure.

$^1$H NMR, 500 MHz (DMSO-d6, 25° C.): 1.75-2.2 ppm (m, 6H), 3.00-4.70 ppm (m, 34H), 8.0-8.6 ppm (m, 4H)

Example 17

5,5'-(2,4-dihydroxypentane-1,5-diyl)bis(acetylazanediyl)bis(N$^1$-(1,3-dihydroxypropan-2-yl)-N$^3$-(2,3-dihydroxypropyl)-2,4,6-triiodoisophthalamide)

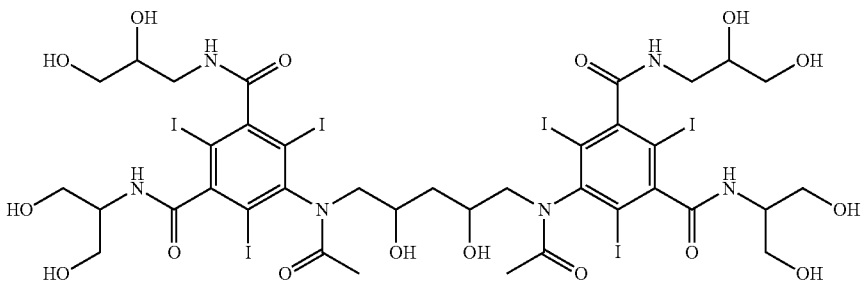 [SMILES: CC(=O)N(CC(O)CC(O)CN(C(C)=O)c1c(I)c(C(=O)NCC(O)CO)c(I)c(C(=O)NC(CO)CO)c1I)c1c(I)c(C(=O)NCC(O)CO)c(I)c(C(=O)NC(CO)CO)c1I]

a) 5-amino-N$^1$-(1,3-dihydroxypropan-2-yl)-N$^3$-(2,3-dihydroxypropyl)-2,4,6-triiodoisophthalamide

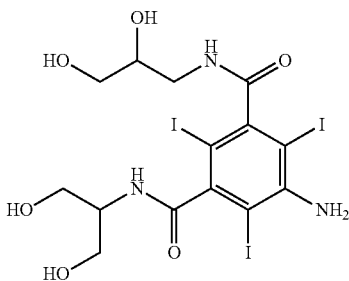 [SMILES: Nc1c(I)c(C(=O)NCC(O)CO)c(I)c(C(=O)NC(CO)CO)c1I]

At 2° C. a mantled reactor with mechanical stirrer, dropping funnel and inner thermometer was charged with DMA (640 ml), triethylamine (224 ml, 161.3 g, 1.59 mol) and 5-Amino-2,4,6-triiodo-isophthalic acid dichloride (320 g, 537 mmol). The mixture was stirred and cooled to −24° C. A solution of 1-amino-2,3-dihydroxypropane (49.92 g, 548 mmol) in DMA (160 ml) was added slowly to keep the inner temperature below −19° C. The mixture was stirred at a temperature gradient from −24° C. to 0° C. in 24 h. A solution of serinol (60 g, 658 mmol) in DMA (160 ml) was added slowly and the mixture was stirred at a temperature gradient from 0° C. to 40° C. in 20 h. The mixture was stirred at 22° C. for 1 day and precipitated triethylamine hydrochloride was filtered off. Evaporation at 60° C./25 mbar left a viscous liquid residue (586 g) which was diluted with water (350 ml). Salts and excess amines were removed by treatment with ion exchangers Amberlite200C (143 ml), IRA67 (148 ml) and IRA900 (56 ml) followed by filtration. The ion exchangers were washed with water (2×400 ml). Some seeding crystals were added to the combined aqueous phase and the solution was stirred slowly at 22° C. for 9 days. The precipitate was isolated by filtration. The filter cake was re-suspended in water (240 ml) and stirred for 1 day. The suspension was filtered and the filter cake was dried in air (216 g, 57% yield, 88.6% HPLC purity). The crude product was purified by preparative HPLC (column: selfpacked Luna C18, 10 μm 250×100 mm, solvents: A=water and B=acetonitrile; gradient 5-10% B over 10 min, hold 10 min; flow 350 ml/min, UV detection at 244 nm and 254 nm). Relevant fractions were combined and freeze dried to yield 5-amino-N$^1$-(1,3-dihydroxypropan-2-yl)-N$^3$-(2,3-dihydroxypropyl)-2,4,6-triiodo-isophthalamide.

LC-ESI-MS) m/z 705.9 [M+H]$^+$ corresponding to the wanted structure.

1H-NMR 500 MHz (solvent: DMSO-d6, ref. TMS): side chain 1: 8.34 ppm (m, NH), 7.91 ppm (m, NH), 4.8-4.4 ppm (m, OH), 3.70 ppm (m, CH), 3.49 ppm (m, CH2), 3.39 ppm (m, CH2), 3.31 ppm (m, NCH2), 3.14 ppm (m, NCH2), side chain 2: 8.09 ppm (d, NH), 7.58 ppm (m, NH), 4.8-4.4 ppm (m, OH), 3.82 ppm (m, CH), 3.65 ppm (m, CH2), 3.53 ppm (m, CH2), side chain 3: 5.46 ppm (m, NH2).

b) Acetic acid 2-acetoxy-3-[3-(2-acetoxy-1-acetoxymethyl-ethylcarbamoyl)-5-diacetylamino-2,4,6-triiodo-benzoylamino]-propyl ester

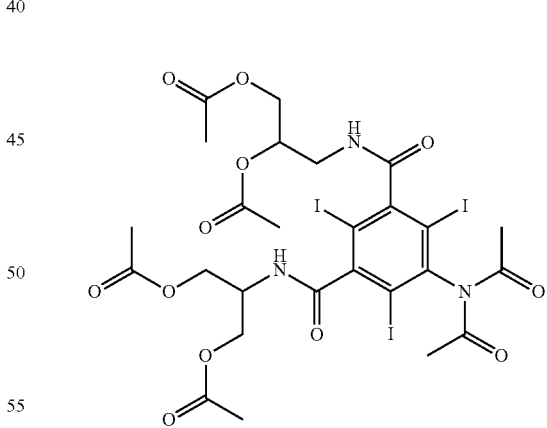

At 23° C. a 2 L 3-neck flask with magnetic stirrer and inner thermometer was filled with acetic anhydride (126 ml, 16.8 eqv.), acetic acid (300 ml, 66.2 eqv.), acetyl chloride (0.562 ml, 0.1 eqv.) and NC100181 (60 g, 1.0 eqv.). The mixture was heated to 100° C. for 18 h and a clear slight brown solution was formed. The reaction mixture was evaporated to dryness at 60° C./17 mbar leaving Acetic acid 2-acetoxy-3-[3-(2-acetoxy-1-acetoxymethyl-ethylcarbamoyl)-5-diacetylamino-2,4,6-triiodo-benzoylamino]-propyl ester (79.8 g) in quantitative yield.

HPLC (Column: YMC AM-302-5, 15 cm, ID 4.6 mm; solvents: A=water, B=50% aqueous acetonitrile, Flow: 1.25 ml/min; gradient 0 min 6% B, 3 min 6% B, 6 min 14% B, 16 min 14% B, 21 min 27% B, 28 min 90% B, 32 min 90% B, 32.1 min 6% B, 40 min 6% B; UV detection at 254 nm): Ret. time=27.7 min (39.1%) and 30.5 min (39.1%).

c) 5,5'-(2,4-dihydroxypentane-1,5-diyl)bis(acetylazanediyl)bis($N^1$-(1,3-dihydroxypropan-2-yl)-$N^3$-(2,3-dihydroxypropyl)-2,4,6-triiodoisophthalamide)

A 250 ml mantled reactor fitted with thermometer, stirring bar, dropping funnel and pH-electrode was cooled by a cryostat to 10° C. Into the reactor was charged methanol (19.9 ml), water (41.4 ml) and boric acid (3.26 g, 52.7 mmol, 2 eqv). The starting material, Acetic acid 2-acetoxy-3-[3-(2-acetoxy-1-acetoxymethyl-ethylcarbamoyl)-5-diacetylamino-2,4,6-triiodo-benzoylamino]-propyl ester (example 17b) (26.6 g, 26.4 mmol, 1 eqv) was added and a drop wise addition of 10 M potassium hydroxide (11.4 g, 184.7 mmol, in 18 ml water) was started to maintain the pH within 12.5-12.8 while keeping the temperature between 10-14° C. After 22 h 2-(oxiran-2-ylmethyl)oxirane (1.34 g, 13.38 mmol, 0.507 eqv) was added while maintaining the pH at 12.5-12.8 with occasional addition of either potassium hydroxide (10 M) or solid boric acid. The temperature was maintained at 10° C. for 28 h and raised to 20° C. for 1 h. After a second addition of 2-(oxiran-2-ylmethyl)oxirane (0.88 g, 8.79 mmol, 0.333 eqv) the mixture was stirred at 20° C. for 23 h. After a third addition of 2-(oxiran-2-ylmethyl)oxirane (0.91 g, 9.09 mmol, 0.345 eqv) the mixture was stirred at 20° C. for 26 h and at 10° C. for 3d keeping the pH within 12.5-12.8. The reaction mixture was quenched by addition of hydrochloric acid (6 M, 14 ml) to attain a pH of 7.7. Water (400 ml) was added followed by acidic ion exchanger AMB200C (132 ml, 221 mmol) and the mixture was stirred until pH was 1.2. Basic ion exchanger IRA67 (211 ml, 221 mmol) was added and the mixture was stirred for 2.5 h until pH 5.7. The ion exchangers were filtered off and washed with water (400) in portions. The combined filtrates were evaporated to dryness (45° C./50 mbar) and the crude product (21.0 g) was purified by preparative HPLC (column: Phenomenex Luna C18, 10 μm 248×101 mm, solvents: A=water and B=acetonitrile; gradient 5-15% B in 35 min, hold 5.15% in 19.12 min and 19.23 min and 6.6% in 5 min; flow 300 ml/min, UV detection at 214 nm and 254 nm). After freeze drying 4.7 g 5,5'-(2,4-dihydroxypentane-1,5-diyl)bis(acetylazanediyl)bis($N^1$-(1,3-dihydroxypropan-2-yl)-$N^3$-(2,3-dihydroxypropyl)-2,4,6-triiodoisophthalamide) (22.3.% yield) was obtained.

LC-ESI-MS m/z 1594.5 (MH$^+$) and its sodium adduct. m/z 1468.6 (M-I+H)$^{3O}$ corresponding to the wanted structure.

$^1$H-NMR (solvent: DMSO-d6, ref. TMS) All protons are leading to multiple resonances due to isomerism; 8.6 ppm-7.5 ppm (m, 4H, NH); 5.0 ppm-4.2 ppm (m, 10H, OH); 4.2 ppm-2.8 ppm (m, 26H, CH, CH$_2$); 2.3 ppm-1.3 ppm (m, 8H, CH$_{3endo}$, CH$_{3exo}$, CH$_2$)

$^1$H-NMR (solvent: D$_5$O, ref. H$_2$O=4.8 ppm) All protons are leading to multiple resonances due to isomerism; 4.3 ppm-3.0 ppm (m, 26H, CH, CH$_2$); 2.42 ppm (m, 1.2H, CH$_{3endo}$,), 1.96 ppm (m, 4.7H, CH$_{3exo}$); 2.0 ppm-1.6 ppm (m, 2H, CH$_2$)

Side chain 1 (APD): 4.06 ppm (m, CH); 3.80 ppm, 3.68 ppm (m, CH$_2$OH); 3.59 ppm, 3.47 ppm (m, NCH$_2$)

Side chain 2 (Ser.): 4.19 ppm (m, CH); 3.88 ppm (m, CH$_2$)

Bridge: 2.42 ppm (m, 1.2H, CH$_{3endo}$,), 1.96 ppm (m, 4.7H, CH$_{3exo}$); 2.0 ppm-1.6 ppm (m, 2H, CH$_2$)

$^{13}$C-NMR (solvent: DMSO-d6, ref. DMSO-d6=39.4 ppm) All carbon atoms are leading to multiple resonances due to isomerism;

Side chain 1 (APD): 171.0 ppm-169.2 (CO); 70.4 ppm-69.3 ppm (CHOH); 64.2 ppm-63.4 ppm (CH$_2$OH); 42.8 ppm-42.1 ppm (NCH$_2$)

Side chain 2 (Ser.): 169.2 ppm-168.5 ppm (CO); 59.3 ppm-58.3 ppm (CH$_2$OH); 53.3 ppm-52.5 ppm (NCH)

Bridge: 171.0 ppm-169.2 ppm (CO); 68.1 ppm-67.1 ppm, 66.5 ppm-65.2 ppm (CH); 57.5 ppm-55.7 ppm (NCH$_2$); 42.1 ppm-40.9 ppm (CH$_2$); 22.7 ppm (CH$_{3exo}$), 22.2 ppm (CH$_{3endo}$)

Aromatic Core: 151.4 ppm-150.0 ppm (C—CO); 148.0 ppm-147.1 ppm (C—N); 101.2 ppm-99.0 (C—I); 91.7 ppm

What is claimed is:

1. A compound selected from the group consisting of:
5,5'-(3,3'-oxybis(2-hydroxypropane-3,1-diyl))bis(acetylazanediyl)bis($N^1$,$N^3$-bis(2,3-dihydroxypropyl)-2,4,6-triiodoisophthalamide);
5,5'-(3,3'-oxybis(2-hydroxypropane-3,1-diyl))bis(acetylazanediyl)bis($N^1$,$N^1$,$N^3$,$N^3$-tetrakis(2-hydroxyethyl)-2,4,6-triiodoisophthalamide);
5,5'-(3,3'-oxybis(2-hydroxypropane-3,1-diyl))bis(acetylazanediyl)bis($N^1$,$N^3$-bis(2,3-dihydroxypropyl)-2,4,6-triiodo-$N^1$,$N^3$-dimethylisophthalamide);
5,5'-(2,7-dihydroxyoctane-1,8-diyl)bis(acetylazanediyl)bis($N^1$,$N^1$,$N^3$,$N^3$-tetrakis(2-hydroxyethyl)-2,4,6-triiodoisophthalamide);
5,5'-(5,12-dihydroxy-2,15-dioxo-7,10-dioxa-3,14-diazahexadecane-3,14-diyl)bis($N^1$,$N^1$,$N^3$,$N^3$-tetrakis(2-hydroxyethyl)-2,4,6-triiodoisophthalamide);
5-(N-((4-(3-(N-(3,5-bis(bis(2-hydroxyethyl)carbamoyl)-2,4,6-triiodophenyl)acetamido)-2-hydroxypropyl)-4-hydroxy-6-(hydroxymethyl)tetrahydro-2H-pyran-2-yl)methyl)acetamido)-$N^1$,$N^1$,$N^3$,$N^3$-tetrakis(2-hydroxyethyl)-2,4,6-triiodoisophthalamide;
5,5'-(2,7-dihydroxyoctane-1,8-diyl)bis(acetylazanediyl)bis($N^1$,$N^3$-bis(2,3-dihydroxypropyl)-2,4,6-triiodoisophthalamide);
5,5'-(2,7-dihydroxyoctane-1,8-diyl)bis(acetylazanediyl)bis($N^1$,$N^3$-bis(2,3-dihydroxypropyl)-2,4,6-triiodo-$N^1$,$N^3$-dimethylisophthalamide);
5,5'-(5,12-dihydroxy-2,15-dioxo-7,10-dioxa-3,14-diazahexadecane-3,14-diyl)bis($N^1$,$N^3$-bis(2,3-dihydroxypropyl)-2,4,6-triiodoisophthalamide);
5,5'-(5,12-dihydroxy-2,15-dioxo-7,10-dioxa-3,14-diazahexadecane-3,14-diyl)bis($N^1$,$N^3$-bis(2,3-dihydroxypropyl)-2,4,6-triiodo-$N^1$,$N^3$-dimethylisophthalamide);
5,5'-(2,3,4-trihydroxypentane-1,5-diyl)bis(acetylazanediyl)bis($N^1$,$N^1$,$N^3$,$N^3$-tetrakis(2-hydroxyethyl)-2,4,6-triiodoisophthalamide);
5,5'-(2,3,4-trihydroxypentane-1,5-diyl)bis(acetylazanediyl)bis($N^1$,$N^3$-bis(2,3-dihydroxypropyl)-2,4,6-triiodoisophthalamide);
5,5'-(2,3,4-trihydroxypentane-1,5-diyl)bis(acetylazanediyl)bis($N^1$,$N^3$-bis(2,3-dihydroxypropyl)-2,4,6-triiodo-$N^1$,$N^3$-dimethylisophthalamide);
5,5'-(2,4-dihydroxypentane-1,5-diyl)bis(acetylazanediyl)bis($N^1$,$N^1$,$N^3$,$N^3$-tetrakis(2-hydroxyethyl)-2,4,6-triiodoisophthalamide);
5,5'-(2,3,4-trihydroxypentane-1,5-diyl)bis(acetylazanediyl)bis($N^1$-(2,3-dihydroxypropyl)-$N^3$-(2-hydroxyethyl)-2,4,6-triiodoisophthalamide);
5,5'-(2,4-dihydroxypentane-1,5-diyl)bis(acetylazanediyl)bis($N^1$-(1,3-dihydroxypropan-2-yl)-$N^3$-(2-hydroxyethyl)-2,4,6-triiodoisophthalamide); and 5,5'-(2,4-dihydroxypentane-1,5-diyl)bis(acetylazanediyl) bis($N^1$-(1,3-dihydroxypropan-2-yl)-$N^3$-(2,3-dihydroxypropyl)-2,4,6-triiodoisophthalamide).

2. A diagnostic agent comprising a compound of claim 1.

3. A diagnostic composition comprising a compound of claim 1 and a pharmaceutically acceptable carrier or excipient.

4. An X-ray diagnostic composition comprising a compound of claim 1 and a pharmaceutically acceptable carrier or excipient.

5. A method of diagnosis comprising the steps of:
administering a compound of claim 1 to a human or animal body;
examining the body with a diagnostic device; and
compiling data from the examination.

6. A method of imaging comprising the steps of:
administering a compound of claim 1 to a human or animal body;
examining the body with a diagnostic device;
compiling data from the examination; and optionally analysing the data.

7. A method of imaging according to claim 6 wherein the method of imaging is X-ray imaging.

\* \* \* \* \*